(12) United States Patent
McKinney et al.

(10) Patent No.: US 6,426,331 B1
(45) Date of Patent: Jul. 30, 2002

(54) INHIBITORS OF STAT FUNCTION

(75) Inventors: Judi McKinney, Mill Valley; Brian C. Raimundo, San Francisco; Timothy D. Cushing, Pacifica, all of CA (US); Hiromitsu Yoshimura, Saitama (JP); Yutaka Ohuchi, Saitama (JP); Akira Hiratate, Saitama (JP); Hiroshi Fukushima, Saitama (JP)

(73) Assignee: Tularik Inc., South San Francisco, CA (US)

( * ) Notice: Subject to any disclaimer, the term of this patent is extended or adjusted under 35 U.S.C. 154(b) by 0 days.

(21) Appl. No.: 09/349,208

(22) Filed: Jul. 7, 1999

Related U.S. Application Data

(60) Provisional application No. 60/092,098, filed on Jul. 8, 1998.

(51) Int. Cl.[7] .................................................. C07K 5/06
(52) U.S. Cl. .......................................... 514/19; 435/7.1
(58) Field of Search ............................. 514/19; 435/7.1

(56) References Cited

FOREIGN PATENT DOCUMENTS

| WO | 97 05162 A | 2/1997 |
|----|-----------|--------|
| WO | 98 31704 A | 7/1998 |
| WO | 99 50283 A | 10/1999 |

OTHER PUBLICATIONS

Martin, Neuropeptides 6, 293, 1985.*
Yao Betty Bei et al., "Direct interaction of STAT4 with the IL-12 receptor." Archives of Biochemistry and Biophysics, vol. 368, No. 1, Aug. 1, 1999, pp. 147–155.

* cited by examiner

*Primary Examiner*—Christopher S. F. Low
*Assistant Examiner*—David Lukton
(74) *Attorney, Agent, or Firm*—Townsend and Townsend and Crew LLP

(57) ABSTRACT

Compounds, compositions and methods that are useful in the treatment of immunoregulatory conditions and disorders are provided herein. In particular, the invention provides compounds which modulate the function of a Signal Transducer and Activator of Transcription (STAT) protein. The compounds are represented by the general formula:

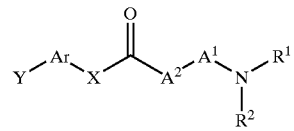

wherein Y, Ar, X, $A^2$, $A^1$, $R^1$ and $R^2$ are defined herein. The compounds are useful to treat, for example, allergic and inflammatory conditions and disorders.

62 Claims, 3 Drawing Sheets

INHIBITORS OF STAT FUNCTION

This application claims the benefit of U.S. provisional application No. 60/092,098, filed Jul. 8, 1999.

FIELD OF THE INVENTION

The present invention relates generally to dipeptide compounds and, more particularly, to novel dipeptide analogs and compositions, their preparation and their use as modulators of the immune system.

BACKGROUND OF THE INVENTION

New therapeutic and diagnostic agents have begun to emerge from discovery efforts which use high-throughput screening directed to certain gene-specific transcription factors.

One family of transcription factors responsible for transmitting a signal to a cell's nucleus are the proteins known as Signal Transducers and Activators of Transcription (STATs; see: Darnell et al. (1994) Science 264: 1415; for review, see: e.g., Ihle et al. (1994) Trends Biochem. Sci. 19:222; Mile et al. (1995) Trends Genetics 11:69; and Horvath et al. (1997) Curr Opn Cell Biol, 9:233). STATs are activated by contact with the phosphorylated cytokine receptor, activation results in the STAT polypeptides forming a dimer and entering the nucleus, where the STAT dimer binds to the regulatory region of a gene that is inducible by the particular cytokine. Binding of the activated STAT dimer triggers transcription of the gene.

The STAT polypeptides (STAT1, STAT2, STAT4, STAT5a, STAT5b, and STAT6) have molecular masses from 84–113 kDa Each STAT protein contains a Src homology-2 (SH2) domain capable of recognizing one or more phosphotyrosine sequences in the cytoplasmic portion of the activated receptor (Shuai et al. (1993) Nature 366: 580). Additionally, each cytokine receptor is specific for a particular STAT protein, and each STAT activates transcription of certain genes, thereby providing two layers of specificity in cytokine-induced signaling.

STAT6 and STAT4 are two proteins that are intimately involved in regulation of immune responses. STAT4 transduces to the nucleus signals from the IL-12 receptor. IL-12 is involved in the development of a $T_H1$ immune response (Kaplan et al. (1996) Nature 382: 174–177), which is part of an organism's defense against intracellular pathogens. IL-12 is also necessary for the T-cell-independent induction of the cytokine interferon (IFN)-γ, which is a key step in the initial suppression of bacterial and parasitic infections. Knockout mice which lack STAT4 were found to be defective in all IL-12 functions tested, including the induction of IFN-gamma, mitogenesis, enhancement of natural killer cytolytic function and $T_H1$ differentiation (Thierfelder et al. (1996) Nature 382: 171–174).

IL-4 signals are transduced to the nucleus by STAT6. IL-4 is a key cytokine in the initiation of a $T_H2$ immune response, and also activates B and T lymphocytes. STAT6-deficient mice were shown to be deficient in IL-4 activities (Kaplan et al. (1996) Immunity 4: 313–319; Takeda et al. (1996) Nature 380: 627–630; Shimoda et al. (1996) Nature 380: 630–633).

Because of the importance of STAT4 and STAT6 in modulating the immune response of an organism, both in response to infection and in undesirable conditions such as inflammation, allergic reactions, and autoimmune diseases, a need exists by which the clinician can diagnose, enhance or reduce STAT4 and STAT6 signals. Intervention at the STAT level would have significant advantages compared to previous approaches, which typically target the IL-4 or IL-12 cytokine itself, or the interaction of the cytokine with the receptor. Disruption of cytokine function itself can cause a variety of undesirable side effects. These can be avoided by intervening at the level of STAT-mediated signal transduction. However, identification of agents that can modulate STAT4 and STAT6-mediated signal transduction has heretofore been hampered by the lack of suitable assays. Recently, a new assay for identification of STAT6 and STAT4 signaling modulators was described (see, U.S. Pat. No. 6,207,391). Assay of binding of STAT4 and STAT6 to their corresponding receptors, and identification of agents which increase or decrease the degree of such binding, has now led to the identification of compounds which are useful in the diagnosis and treatment of various STAT-dependent conditions.

SUMMARY OF THE INVENTION

In one aspect, the present invention provides compounds which are represented by the formula:

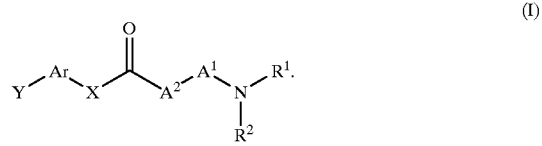

(I)

In the above formula, $R^1$ and $R^2$ and are each independently selected from hydrogen, $(C_1-C_8)$alkyl, aryl, aryl $(C_1-C_8)$alkyl, $(C_1-C_8)$heteroalkyl and aryl$(C_1-C_8)$ heteroalkyl, with the proviso that at least one of $R^1$ and $R^2$ is selected from aryl, aryl$(C_1-C_8)$alkyl and aryl$(C_1-C_8)$ heteroalkyl.

The symbol $A^1$ represents an L-α-amino acid, D-α-amino acid or a radical having the formula:

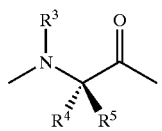

in which $R^3$ is hydrogen or $(C_1-C_8)$ alkyl, and $R^4$ and $R^5$ are each independently selected from hydrogen, $(C_1-C_8)$alkyl and $(C_1-C_8)$heteroalkyl, or $R^4$ and $R^5$ can be individually combined with $F^3$ to form a 5-, 6-, 7- or 8-membered ring containing from one to three heteroatoms.

The symbol $A^2$ represents an L-α-amino acid, D-α-amino acid or a radical having the formula:

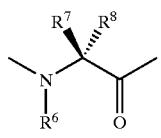

In the indicated formula, $R^6$ is either hydrogen or $(C_1-C_4)$ alkyl; $R^7$ and $R^8$ are independently selected from hydrogen, $(C_1-C_8)$alkyl and $(C_1-C_8)$heteroalkyl, or $R^7$ and $R^8$ can be combined with each other to form a 5-, 6, 7- or 8-membered ring containing from zero to three heteroatoms.

The letter X represents a bond, a $(C_1-C_4)$ saturated or unsaturated alkyl linking group or a $(C_1-C_4)$ saturated or unsaturated heteroalkyl linking group. Ar represents an aryl group.

The letter Y represents an acidic moiety, an isostere of an acidic moiety or an ester of an acidic moiety that can be converted to an acidic moiety in vivo. The acidic moiety (or ester or isostere) is attached to Ar either directly or with a spacer. Accordingly, Y can be represented as a radical of formula:

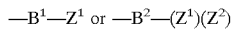

wherein $B^1$ is a bond or a divalent linking group and $B^2$ is a trivalent linking group. The remaining groups, $Z^1$ and $Z^2$ are as follows:

$Z^1$ represents a member selected from $—CO_2R^9$, $—P(O)(OR^9)(OR^{10})$, $—P(O)(R^9)(OR^{10})$, $—S(O)_2(OR^9)$, $—S(O)(OR^9)$ and a carboxylic acid isostere. Similarly, the symbol $Z^2$ represents a member selected from $—CO_2R^9$, $—NHR^{11}$, $—P(O)(OR^9)(OR^{10})$, $—P(O)(R^9)(OR^{10})$, $—S(O)_2(OR^9)$, $—S(O)(OR^9)$ and a carboxylic acid isostere. For the listed $Z^1$ and $Z^2$ groups, $R^9$ and $R^{10}$ each independently represent H, $(C_1–C_8)$alkyl or $(C_1–C_8)$heteroalkyl; and $R^{11}$ represents $(C_1–C_8)$alkyl.

The compounds of the present invention are useful in compositions that further comprise a pharmaceutically acceptable excipient Both the compounds and compositions of the present inventions are useful for the diagnosis and treatment (including prophylactic treatment) of conditions mediated through STAT signaling. Examples of conditions associated with STAT signaling include, but are not limited to: Th1-mediated conditions such as delayed-type hypersensitivity, contact dermatitis, uveitis, Crohn's disease, psoriasis and autoimmune diseases (typically associated with STAT4 signaling);

Th2-mediated diseases such as allergic rhinitis, asthma, scleroderma, eczema and conjunctivitis (typically associated with STAT6 signaling); proliferative disorders such as cancers (associated with STAT3 and/or STAT5 signaling); and STAT1 conditions which are similar to those described for STAT4, but typically observed in more acute situations such as acute-transplant rejections. A variety of additional conditions associated with STAT signaling include atopic dermatitis, anaphylaxis, food or drug induced allergy, hypersensitivity reactions, alveolitis, Churg-Strauss syndrome, urticaria, angiodema, and systemic lupus erythematosus.

Other objects, features and advantages of the present invention will be apparent to one of skill in the art from the following detailed description and the claims.

DETAILED DESCRIPTION OF THE INVENTION

Abbreviations

Figure 1:
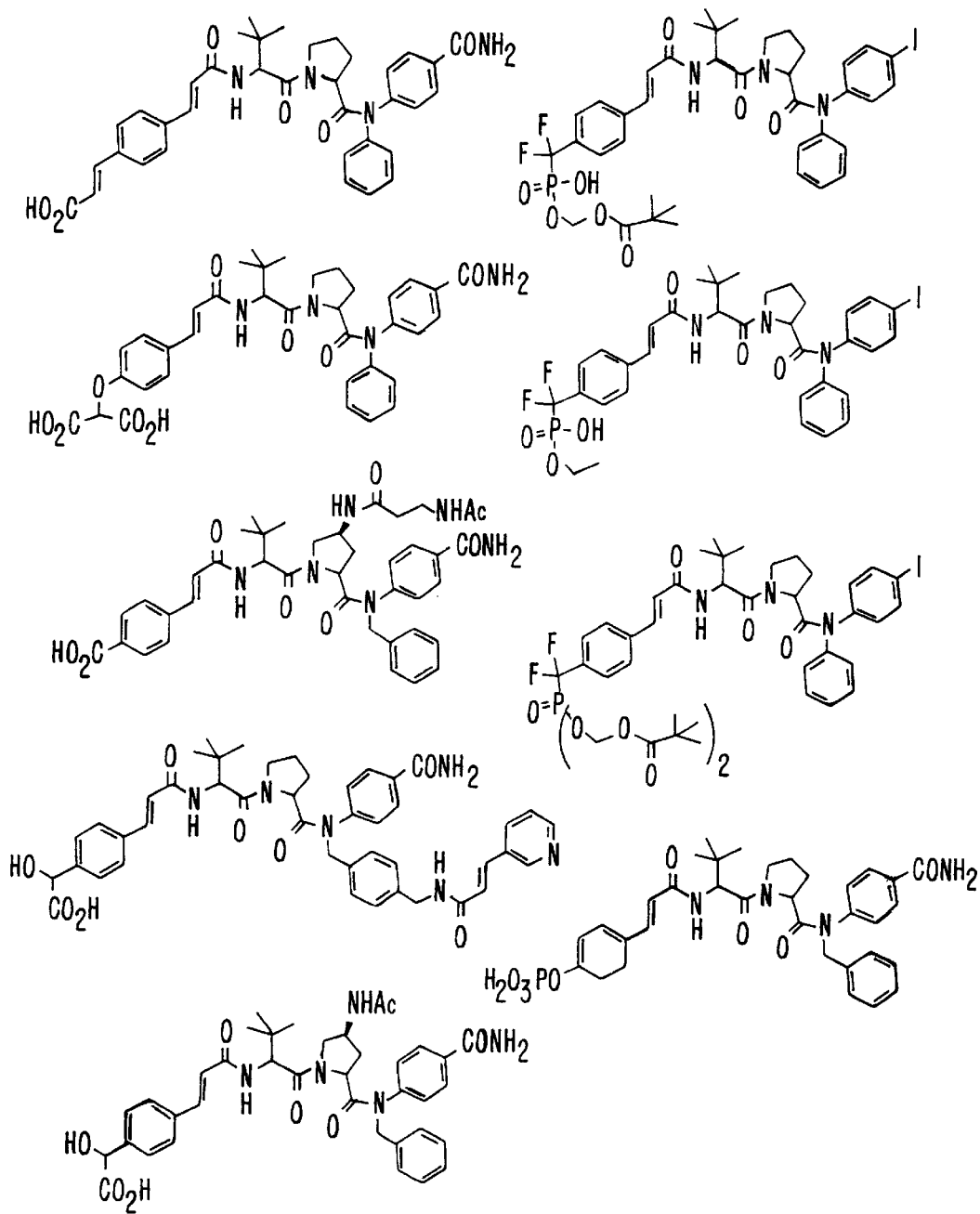
FIG. 1 provides the structures for certain particularly preferred compounds of the present invention.

The following abbreviations are used herein: Ac, acetyl; Bn, benzyl; Bz, benzoyl; Boc, t-butoxycarbonyl; EDC, 1-(3-Dimethylaminopropyl)-3-ethylcarbodiimide hydrochloride; HOBT, hydroxybenzotriazole; NMM, N-methylmorpholine; DMF, dimethylformamide; EtOAc, ethyl acetate; HBTU, 2-(1H-benzotriazole-1-yl)-1,1,3,3-tetramethyluronium hexafluorophosphate; THF, tetrahydrofuran; FMOC, fluorenylmethyloxycarbonyl; TFA, trifluoroacetic acid; Me, methyl; Et, ethyl; Ph, phenyl;

STAT, signal transducers and activators of transcription;

Definitions

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multi-radicals, having the number of carbon atoms designated (i.e. $C_1–C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "cycloalkyl" and "alkylene." The term "alkylene" by itself or as part of another substituent means a divalent radical derived from an alkane, as exemplified by $—CH_2CH_2CH_2—$. Typically, an allyl group will have from 1 to 24 carbon atoms, with those groups having 10 or fewer carbon atoms being preferred in the present invention. A "lower alkyl" or "lower alkylene" is a shorter chain alkyl or allylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quatermized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include $—CH_2—CH_2—O—CH_3$, $—CH_2—NH—CH_3$, $—CH_2—CH_2—N(CH_3)—CH_3$, $—CH_2—S—CH_2—CH_3$, $—CH_2—CH_2—S(O)—CH_3$, $—CH_2—CH_2—S(O)_2—CH_3$, $—CH=CH—O—CH_3$, $—Si(CH_3)_3$, $—CH_2—CH=N—OCH_3$, and $—CH=CH—N(CH_3)—CH_3$. Up to two heteroatoms may be consecutive, such as, for example, $—CH_2—NH—OCH_3$ and $—CH_2—O—Si(CH_3)_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by $—CH_2—CH_2—S—CH_2CH_2—$ and $—CH_2—SH—CH_2—NH—CH_2—$. For heteroalkylene groups, heteroatoms can also occupy either or both of the chain termini. Still further, for alkylene and heteroalkylene linking groups, as well as all other linking groups described herein, no specific orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2, 5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quatermized The aryl groups that contain heteroatoms may be referred to as "heteroaryl" and can be attached to the remainder of the molecule through a heteroatom. Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5quinoxalinyl, 3quinolyl, and 6quinolyl. Substituents for each of the above noted aryl ring systems are selected from the group of acceptable substituents described below.

The terms "arylalkyl" and "arylheteroalkyl" are meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 1-naphthyloxy-3-propyl, and the like). The arylalkyl and arylheteroalkyl groups will typically contain from 1 to 3 aryl moieties attached to the alkyl or heteroalkyl portion by a covalent bond or by fusing the ring to, for example, a cycloalkyl or heterocycloalkyl group. For arylheteroalkyl groups, a heteroatom can occupy the position at which the group is attached to the remainder of the molecule. For example, the term "arylheteroalkyl" is meant to include benzyloxy, 2-phenylethoxy, phenethylamine, and the like.

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —CO$_2$R', —CONR'R", —OC(O)NR'R", —NR"C(O)R', —NR"C(O)$_2$R', —NH—C(NH$_2$)=NH, —NH—C(NH$_2$)=NR', —S(O)R', —S(O)$_2$R', —S(O)$_2$NR'R", —CN and —NO$_2$ in a number ranging from zero to (2N+1), where N is the total number of carbon atoms in such radical, and R', R"and R'" each independently refer to hydrogen, unsubstituted(C$_1$–C$_8$)alkyl and heteroalkyl, unsubstituted aryl, aryl substituted with 1–3 halogens, unsubstituted alkyl, alkoxy or thioalkoxy groups, or aryl-(C$_1$–C$_4$)alkyl groups. Additionally, when R' and R" are attached to the same nitrogen atom, they can be combined with the nitrogen atom to form a 5-, 6-, or 7-membered ring. For example, —NR'R" is meant to include 1-pyrrolidinyl and 4morpholinyl. From the above list of substituents, one of skill will understand that the term, for example, (C$_1$–C$_8$) alkyl, is meant to include groups which are commonly referred to as (C$_1$–C$_8$)acyl (e.g., acetyl, propionyl, butanoyl, hexanoyl, and the like).

Similarly, substituents for the aryl groups are varied and are selected from: -halogen, —OR', —OC(O)R', —NR'R", —SR', —R', —CN, —NO$_2$, —CO$_2$R', —CONR'R", —OC(O)NR'R", —NR"C(O)R', —NR"C(O)$_2$R', —NH—C(NH$_2$)=NH, —NR' C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, in a number ranging from zero to the total number of open valences on the aromatic ring system; and where R' and R" are independently selected from hydrogen, (C$_1$–C$_8$)alkyl and heteroalkyl, unsubstituted aryl, (unsubstituted aryl)-(C$_1$–C$_4$) alkyl, and (unsubstituted aryl)oxy-(C$_1$–C$_4$)alkyl.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'—or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$), —X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the termr "heteroatom" is meant to include oxygen (O), nitrogen (N), sulfur (S) and silicon (Si).

For the compounds of the invention which contain amino acids, the amino acids will include any of the gene-encoded amino acids (e.g., Ala, Arg, Asn, Asp, Cys, Gln, Glu, Gly, His, Ile, Leu, Lys, Met, Pro, Ser, Thr, Trp, Tyr, and Val) as well as commonly encountered amino acids which are not gene-encoded. Examples of some useful non-gene-encoded amino acids and their abbreviations are ornithine (Orn); t-butylglycine (t-BuG); phenylglycine (PhG); cyclohexyla-lanine (Cha); norleucine (Nle); 2-naphthylalanine (2-Nal), and homoarginine (Har).

All of the amino acids used in the present invention may be either the D- or L-isomer. The L-isomers are preferred unless otherwise noted.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of formula I. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds.

For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Still further, the compounds of the present invention can be conjugated to easily-detectable groups, such as fluorescein or biotin, for use as reagents or diagnostic tools. Additionally, such tagged compounds can be further attached to a solid support (e.g., bead, resin or microtiter plate) and used in binding experiments to discover other compounds that interact with STAT6.

General

The present invention provides compounds, compositions and methods for the inhibition or treatment of conditions or disorders modulated by the STAT transcription factors, particularly STAT4 and STAT6. Additionally, the compounds are useful for the diagnosis of conditions dependent on STAT signaling. Without intending to be bound by a theory, it is believed that certain compounds of the present invention block interaction between phosphorylated tyrosine residues in the IL-4 receptor and the $SH_2$ domain of STAT6. In this manner, phosphorylation (i.e., activation) of STAT6 by IL-4-receptor-associated kinases is prevented. It is also believed that the compounds exert their effect by interfering with the dimerization of STAT6 monomers that is required before the STAT6 dimer can bind to the STAT6-dependent genes and initiate transcription of, for example, germline epsilon transcript. In view of this transcriptional control, the compounds, compositions and methods of the present invention will be useful in treating (suppressing or inhibiting) the full spectrum of immune disorders which require transcriptional activation by STAT6 dimer, including allergic conditions (e.g., allergic rhinitis, asthma, atopic dermatitis, contact dermatitis, anaphylaxis, food or drug induced allergy, conjunctivitis, uveitis, hypersensitivity reactions, alveolitis and psoriasis), Churg-Strauss syndrome, delayed-type hypersensitivity, urticaria, angiodema, eczema, scleroderma, and systemic lupus erythematosus.

EMBODIMENTS OF THE INVENTION

Compounds

In one aspect, the present invention provides compounds which are represented by the formula:

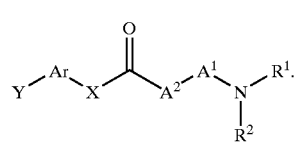

(I)

In the above formula, $R^1$ and $R^2$ are each independently selected from hydrogen, $(C_1-C_8)$alkyl, aryl, aryl$(C_1-C_8)$ alkyl, $(C_1-C_8)$heteroalkyl and aryl$(C_1-C_8)$heteroalkyl, with the proviso that at least one of $R^1$ and $R^2$ is selected from aryl, aryl$(C_1-C_8)$alkyl and aryl$(C_1-C_8)$heteroalkyl.

In one group of embodiments, $R^1$ is selected from $(C_1-C_8)$alkyl and $(C_1-C_8)$heteroalkyl, and $R^2$ is selected from aryl, aryl$(C_1-C_8)$alkyl, and aryl$(C_1-C_8)$heteroalkyl. More preferably, $R^2$ is selected from aryl and aryl$(C_1-C_8)$ alkyl. Most preferred are those embodiments in which $R^2$ is an optionally substituted phenyl or optionally substituted benzyl group.

In another group of embodiments, $R^1$ and $R^2$ are each selected from aryl, aryl$(C_1-C_8)$alkyl and aryl$(C_1-C_8)$ heteroalkyl. In one group of particularly preferred embodiments, $R^1$ and $R^2$ are each independently an optionally substituted phenyl group. In still other preferred embodiments, $R^1$ and $R^2$ are both optionally substituted benzyl groups. In yet other preferred embodiments, $R^1$ is an optionally substituted phenyl group and $R^2$ is an optionally substituted benzyl group. With the embodiments described herein, the substituents on the aryl rings can be any of those substituents described above in the definitions section. Preferably, however, the substituents are selected from —CON, —CH$_2$NCO—(4-nitro-2-pyrazolyl), —CONHPh, —CH$_2$NH$_2$. —CH$_2$NHCO—CH=CH-(3-nitrophenyl), —CH$_3$, —Cl, —I, —CO$_2$H, —CO$_2$CH$_3$, —OCH$_3$, —OH, —Ph, —OPh, —CON(CH$_3$)$_2$, —C(CH$_3$)$_3$, —CH$_2$NHAc, —CN, —CH$_2$NHCO—CH=CH—(4-pyridyl), and the like. In certain preferred embodiments, $R^1$ and $R^2$ are phenyl or benzyl groups and the additional substituents occupy positions on the benzene ring that are meta or para to the positions at which the benzene rings are attached to the remainder of the molecule.

In formula (I), the symbol $A^1$ represents an L-α-amino acid, D-α-amino acid or a radical having the formula:

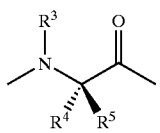

in which $R^3$ is hydrogen or (C$_1$–C$_4$) alkyl, and $R^4$ and $R^5$ are each independently selected from hydrogen, (C$_1$–C$_8$)alkyl and (C$_1$–C$_8$)heteroalkyl, or $R^4$ and $R^5$ can be individually combined with $R^3$ to form a 5-, 6-, 7- or 8-membered ring containing from one to three heteroatoms. One of skill in the art will understand that when $A^1$ is described as an amino acid, what is meant is a residue of the amino acid that typically remains upon incorporation of the amino acid into a peptide or other similar linear array or polymer. For example, if $A^1$ is "alanine," the term is meant to refer to that fragment that is typically incorporated into a peptide or protein (ie., —NH—CH(CH$_3$)—C(O)—). In certain preferred embodiments, $A^1$ is an amino acid selected from 2-aminoisobutyric acid, sarcosine, norvaline, homoserine, citrulline, norleucine, 2,3-diaminopropionic acid, methionine oxide, methionine dioxide, penicillarnine, homoleucine, ornithine, 3H-dehydroproline, 2-methylproline, homoproline, 5-phenylproline, 4chloroproline, proline, tyrosine, serine, methionine and alanine.

In another group of preferred embodiments, $A^1$ is a radical having the formula above in which $R^1$ is hydrogen and $R^3$ and $R^4$ are combined to form a 5-, 6-, or 7-membered ring containing from one to three heteroatoms. More preferably, $R^3$ and $R^4$ are combined to form a 5-membered ring containing from one to three heteroatoms. In other preferred embodiments, $A^1$ is a radical selected from

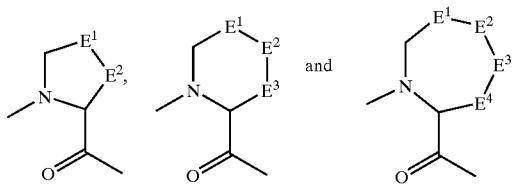

in which $E^1$, $E^2$, $E^3$ and $E^4$ each independently represent C, N, S or O, with the proviso that the 5-, 6- or 7-membered ring contains no more than three heteroatoms as ring members. When any of $E^1$ to $E^4$ are C or N, the remaining valences can be occupied by bonds to hydrogen, aryl, (C$_1$–C$_8$)alkyl, (C$_1$–C$_8$)heteroalkyl, aryl(C$_1$–C$_8$)alkyl, aryl (C$_1$–C$_8$)heteroalkyl, alkylsulfonyl, arylsulfonyl and arylsulfinyl. Preferably, when any of $E^1$ to $E^4$ are N, the remaining valence is occupied by (C$_1$–C$_8$)alkyl, most preferably substituted (C$_1$–C$_8$)alkyl (e.g., acetyl, propionyl and the like).

In one group of particularly preferred embodiments, $A^1$ is represented by the formula:

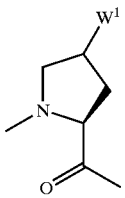

in which $W^1$ represents —OR$^{12}$ or —NR$^{12}$R$^{13}$. The $R^{12}$ and $R^{13}$ groups independently represent hydrogen, aryl, (C$_1$–C$_8$) alkyl, (C$_1$–C$_8$)heteroalkyl, aryl(C$_1$–C$_8$)alkyl, aryl(C$_1$–C$_8$) heteroalkyl, alkylsulfonyl, arylsulfonyl and arylsulfinyl. Preferably, $W^1$ is —NHCOCH$_3$, —NHCOCH$_2$CH$_2$NHAc, —NH$_2$, —NH-tosyl, —NHCOPh, —NHCOCH(CH$_3$)$_2$, —NHSO2CH$_3$, —NHCO$_2$CH$_2$Ph, —N(CH$_3$)$_2$, and —N(CH$_2$Ph)$_2$. The $W^1$ group can have either a cis or trans orientation relative to the carbonyl group at the 2-position of the 5pyrrolidine ring, or can exist as a mixture of isomers at the center bearing the $W^1$ group.

The symbol $A^2$ represents an L-α-amino acid, D-α-amino acid or a radical having the formula:

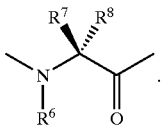

As with $A^1$ above, when $A^2$ is referred to as an amino acid, the description means that portion of an amino acid that remains upon incorporation of the amino acid into the remainder of the molecule. When $A^2$ has the formula indicated, $R^6$ is either hydrogen or (C$_1$–C$_8$)alkyl; $R^7$ and $R^1$ are independently selected from hydrogen, (C$_1$–C$_8$)alkyl and (C$_1$–C$_8$)heteroalkyl, or $R^7$ and $R^8$ can be combined with each other to form a 5-, 6, 7- or 8-membered ring containing from zero to three heteroatoms. In preferred embodiments, $A^2$ represents an amino acid selected from norvaline, homoserine, cyclohexylalanine, norleucine, diaminopropionic acid, methionine oxide, homoleucine, ornithine, tert-butylglycine, 3-methoxyvaline, allothreonine, valine, threonine, leucine, isoleucine, lysine and methionine. More preferably, $A^2$ is selected from L-valine, L-leucine, L-lysine, L-methionine, L-threonine, L-isoleucine and L-tert-butylglycine. Most preferably, $A^2$ is L-valine or L-tert-butylglycine.

In formula (I), the symbol X represents a bond, a (C$_1$–C$_4$) saturated or unsaturated alkyl linking group or a (C$_1$–C$_4$) saturated or unsaturated heteroalkyl linking group. Preferably, X is —OCH$_2$—, —CH$_2$CH$_2$—, —CH=CH—, —CH=C(CH$_3$)—, —NHCH$_2$—, —N(R)CH$_2$CH$_2$—, —N=CH—, or —CH=N— in which R represents hydrogen or a lower alkyl group (e.g., methyl, ethyl, acetyl, propyl and the like). Most preferably, X is a trans —CH=CH— linking group.

The symbol Ar represents an aryl group. A variety of aryl groups are useful in the present invention. Preferred aryl groups include benzene, naphthalene, pyridine, furan, imidazole, pyrazole, thiophene, biphenyl, dihydronaphthalene, 1,2,3-triazole and pyrazine. Particularly preferred is benzene in which the X and Y groups are attached to the benzene ring at positions para to each other. In another group of embodiments, Ar is benzene, X and Y are attached at positions para to each other, and the benzene ring is further substituted with at least one additional substituent selected from -halogen, —OR', —OC(O)R', —NR'R", —SR', —R', —CN, —NO$_2$, —CO$_2$R', —CONR'R", —OC(O)NR'R", —NR"C(O)R', —NR"C(O)$_2$R', perfluoro(C$_1$–C$_4$)alkoxy, and perfluoro(C$_1$–C$_4$alkyl, where R' and R" are independently selected from hydrogen, (C$_1$–C$_8$)alkyl, (C$_1$–C$_8$)heteroalkyl, and unsubstituted aryl.

The letter Y represents an acidic moiety, an isostere of an acidic moiety or an ester of an acidic moiety that can be converted to an acidic moiety in vivo. The acidic moiety (or ester or isostere) is attached to Ar either directly or with a spacer. Accordingly, Y can be represented as a radical of formula:

$$—B^1—Z^1 \text{ or } —B^2—(Z^1)(Z^2)$$

wherein $B^1$ is a bond or a divalent linking group and $B^2$ is a trivalent linking group. The terms "divalent linking group" and "trivalent linking group" are meant to include groups having two and three available valences respectively, for covalent attachment to Ar, $Z^1$ and $Z^2$. The linking groups typically serve as scaffolds to preserve a certain orientation or spacing between $Z^1$ or $Z^2$ and Ar. As a result, the linking groups will typically comprise from one to eight carbon atoms. Optionally, from one to three of the carbon atoms will be replaced with a heteroatom (e.g., O, N S, Si). For example, $B^1$ can be a bond, —O—, —CH$_2$—, —CHF—, —CH(OH)—, —CF$_2$—, —OCH$_2$—, —CH$_2$CH$_2$—, —CH=CH—, —NH—CH$_2$—, —N=CH—, —CF$_2$CF$_2$—, —OCF$_2$—, —OCHF— or —CHF—CHF—. As already noted, $B^1$ can be a longer homolog of the above linking groups, for example a three-carbon or four-carbon alkylene group which is optionally substituted with additional alkyl groups, halogen atoms or heteroatoms. Trivalent ($B^2$) linking groups that are useful in the present invention include, for example,

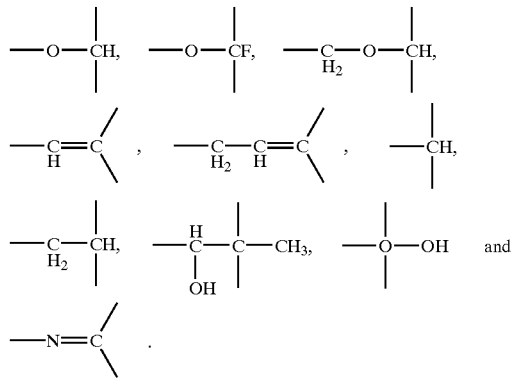

The symbol $Z^1$ represents a member selected from —CO$_2$R$^9$, —P(O)(OR$^9$)(OR$^{10}$), —P(O)(R$^9$)(OR$^{10}$), —S(O)$_2$(OR$^9$), —S(O)(OR$^9$) and a carboxylic acid isostere. Similarly, the symbol Z2 represents a member selected from —CO$_2$R$^9$, —NHR$^{11}$, —P(O)(OR$^9$)(OR$^{10}$), —P(O)(R$^9$)(OR$^{10}$), —S(O)$_2$(OR$^9$), —S(O)(OR$^9$) and a carboxylic acid isostere. For the listed $Z^1$ and $Z^2$ groups, $R^9$ and $R^{10}$ each independently represent H, (C$_1$–C$_8$)alkyl, aryl or (C$_1$–C$_8$)heteroalkyl; and $R^{11}$ represents (C$_1$–C$_8$)alkyl, preferably a substituted (C$_1$–C$_8$)alkyl group (e.g., acetyl, propionyl, butanoyl, and the like).

In one group of preferred embodiments, $Z^1$ and $Z^2$ are selected from —CO$_2$H, —PO$_3$H$_2$, —P(O)(CH$_3$)(OH) and a carboxylic acid isostere. A number of carboxylic acid isosteres are known to those of skill in the art, including, for example, tetrazole, amidotetrazole, methanesulfonamide, 3-isoxazolone and 1,2,4-triazole (see, e.g., Ornstein, et al., *J. Med. Chem.* 39:2232–2244 (1996) and Lipinski, *Ann. Reports Med. Chem.* 21:283–291 (1986). Most preferably, $Z^1$ and $Z^2$ are selected from —CO$_2$H and —PO$_3$H$_2$. For those embodiments in which $Z^1$ is a —CO$_2$H or —PO$_3$H$_2$ (or a salt thereof), $B^1$ will preferably be a bond, —O—, —CH$_2$—, —CHF—, —CH(OH)—, —CF$_2$—, —OCH$_2$—, —CH$_2$CH$_2$—, —CH=CH—, —NH—CH$_2$—, —CF$_2$CF$_2$—, —OCF$_2$—, —OCHF— or —CHF—CHF—.

In another group of preferred embodiments, $Z^1$ and $Z^2$ are selected from —CO$_2$R$^9$, —P(O)(OR$^9$)(OR$^{10}$) and —P(O)(R$^9$)(OR$^{10}$), in which $R^9$ and $R^{10}$ are each independently selected from (C$_1$–C$_8$)alkyl and (C$_1$–C$_8$)heteroalkyl. Suitable alkyl and heteroalkyl groups include, for example, methyl, ethyl, propyl, isopropyl, tert-butyl, sec-butyl, isobutyl, methoxymethyl, methoxyethyl, acetoxymethyl, propionyloxymethyl and pivaloyloxymethyl (—CH$_2$OC(O)C(CH$_3$)$_3$).

The above recitation provides general description of the embodiments and preferred embodiments for portions of the compounds of the present invention. Certain combinations of the components are particularly preferred. For example, in one particularly preferred embodiment, the compounds have the formula:

(II)

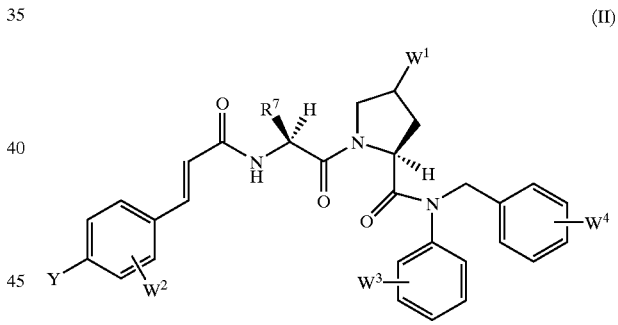

wherein the symbol $W^1$ represents hydrogen, —OR$^{12}$ or —NR$^{12}$R$^{13}$; and the symbols $W^2$, $W^3$ and $W^4$ each independently represent hydrogen, halogen, —R$^{14}$, —CO$_2$R$^{14}$, —OR$^{14}$, —NR$^{14}$R$^{15}$ or —CONR$^{14}$R$^{15}$; wherein each of $R^{12}$, $R^{13}$, $R^{14}$ and $R^{15}$ independently represent hydrogen, aryl, (C$_1$–C$_8$)alkyl, (C$_1$–C$_8$)heteroalkyl, aryl(C$_1$–C$_8$)alkyl, aryl(C$_1$–C$_8$)heteroalkyl, alkylsulfonyl, arylsulfonyl and arylsulfinyl. The remaining symbols, $R^7$ and Y can be any of the groups defined for general formula (I), above. In one group of preferred embodiments, $R^7$ is selected from ethyl, isopropyl, isobutyl, tert-butyl, sec-butyl, cyclohexylmethyl, and 2-methoxy-2-propyl. Also preferred are those embodiments in which Y is selected from:

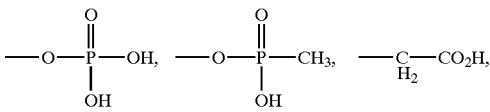

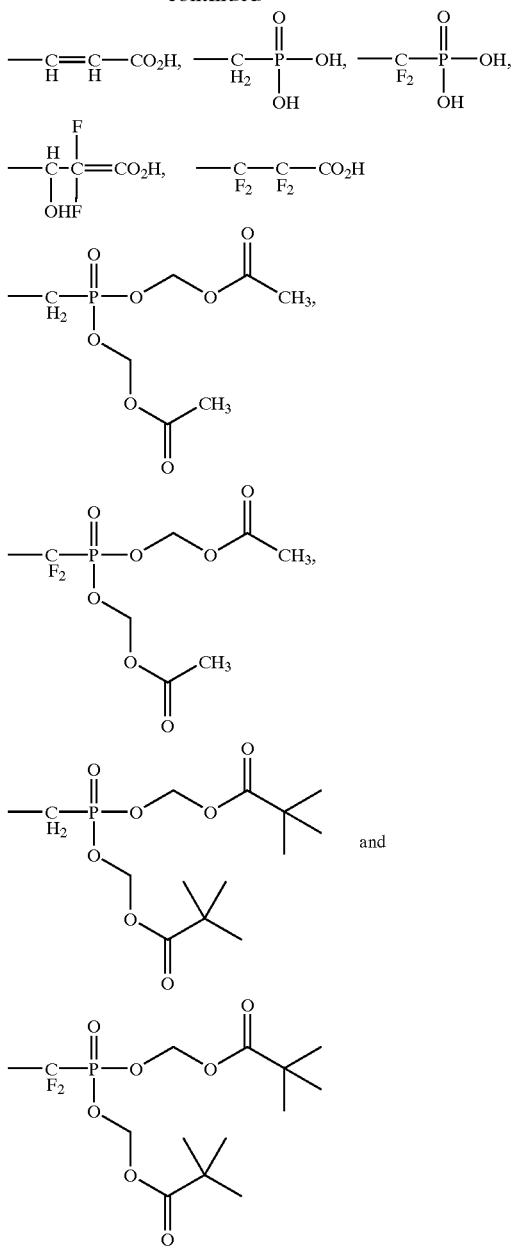

Structural formulae for some of the most preferred compounds of the present invention are provided in FIG. 1.

The compounds of the present invention are useful in therapeutic as well as prophylactic and diagnostic applications, and are also useful in drug discovery research. Accordingly, the present invention provides suitably modified derivatives of the above compound in such a manner that their interaction with a STAT6 molecule (or fragment thereof) can be easily detected by physical or chemical means. The present invention further provides compositions containing the above compounds and pharmaceutically acceptable excipients or diagnostically acceptable excipients. Still further, the invention provides methods of treating conditions mediated by STAT6 signaling including, allergic conditions (e.g., allergic rhinitis, asthma, atopic dermatitis, contact dermatitis, anaphylaxis, food or drug induced allergy, conjunctivitis, uveitis, hypersensitivity reactions, alveolitis and psoriasis), Churg-Strauss syndrome, delayed-type hypersensitivity, urticaria, angiodema, eczema, scleroderma, and systemic lupus erythematosus. In addition to treatments for existing conditions, the present invention also provides methods for prophylactic treatments to prevent the onset of the above-noted disorders in patients.

Preparation of the Compounds

The compounds of the present invention can be prepared as generally described below and depicted in Schemes 1–4. One of skill in the art will appreciate that certain additional steps (e.g., protection and deprotection of certain labile substituents) may be necessary, but are easily accomplished by the skilled artisan.

Scheme 1 provides a general outline for the synthesis of compounds in which $A^1$ is an L-α-amino acid (alanine), $A^2$ is an L-α-amino acid (valine), and $R^1$ and $R^2$ are both aryl groups.

As shown in Scheme 1, treatment of Boc-protected L-alanine (i) with methyl 4-aminobenzoate (ii) in the presence of EDC provides amide iii. Treatment of iii with triphenylbismuth and copper(II) acetate provides diaryl amide iv. Removal of the Boc protecting group from iv and subsequent coupling with Boc-valine, followed by conversion of the methyl ester group to an amide (with ammonia) provides dipeptide v. Again, the removal of the Boc protecting group and acylation of the free amine with the acid vi, furnishes vii after ester hydrolysis (HCl, dioxane).

SCHEME 1

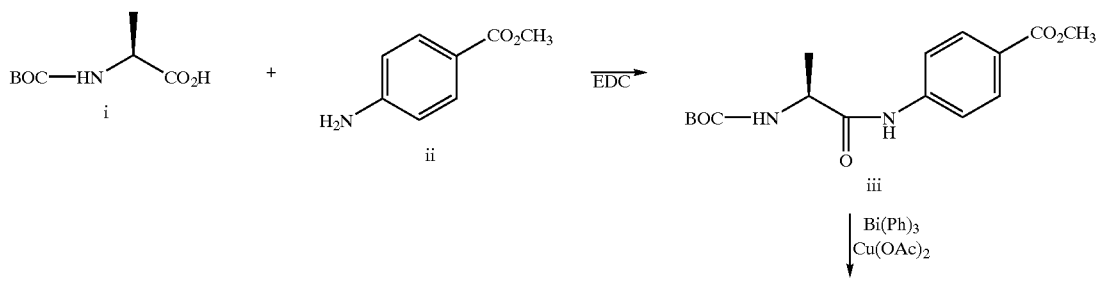

15

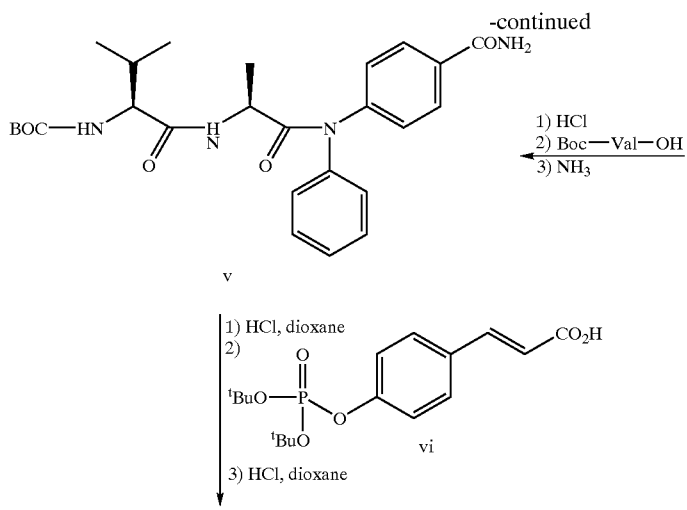

v

16

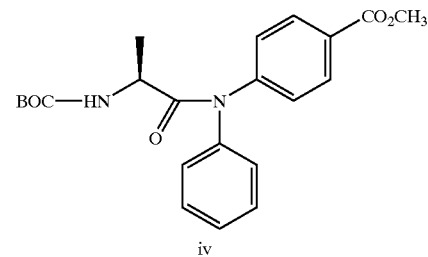

iv

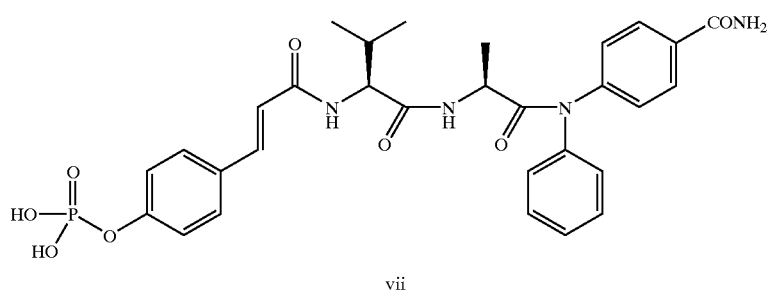

vii

The general methodology outlined in Scheme 1 can be used with essentially any amino acids. For example, compounds of the present invention can be prepared by substituting Boc-alanine (i) with suitably protected forms of any of the following non-limiting examples: 2-aminoisobutyric acid, sarcosine, norvaline, homoserine, citrulline, norleucine, 2,3diaminopropionic acid, methionine oxide, methionine dioxide, penicillarnine, homoleucine, ornithine, 3H-dehydroproline, 2-methylproline, homoproline, 5-phenylproline, 4-chloroproline, proline, tyrosine, serine, and methionine. Similarly, Boc-valine can be substituted with suitably protected forms of, for example, norvaline, homoserine, cyclohexylalanine, norleucine, diaminopropionic acid, methionine oxide, homoleucine, ornithine, tert-butylglycine, 3-methoxyvaline, allothreonine, threonine, leucine, isoleucine, lysine and methionine. Similarly, the acid vi can be replaced in the synthesis scheme with a variety of other acids (see, for example, the acids depicted in Scheme 4 and those prepared in Example 3.3).

SCHEME 2

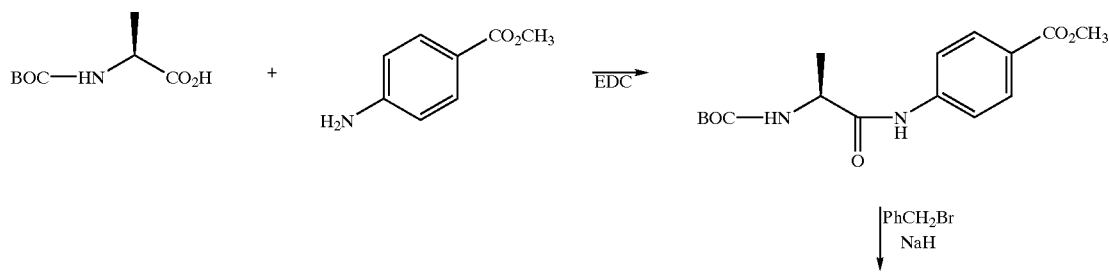

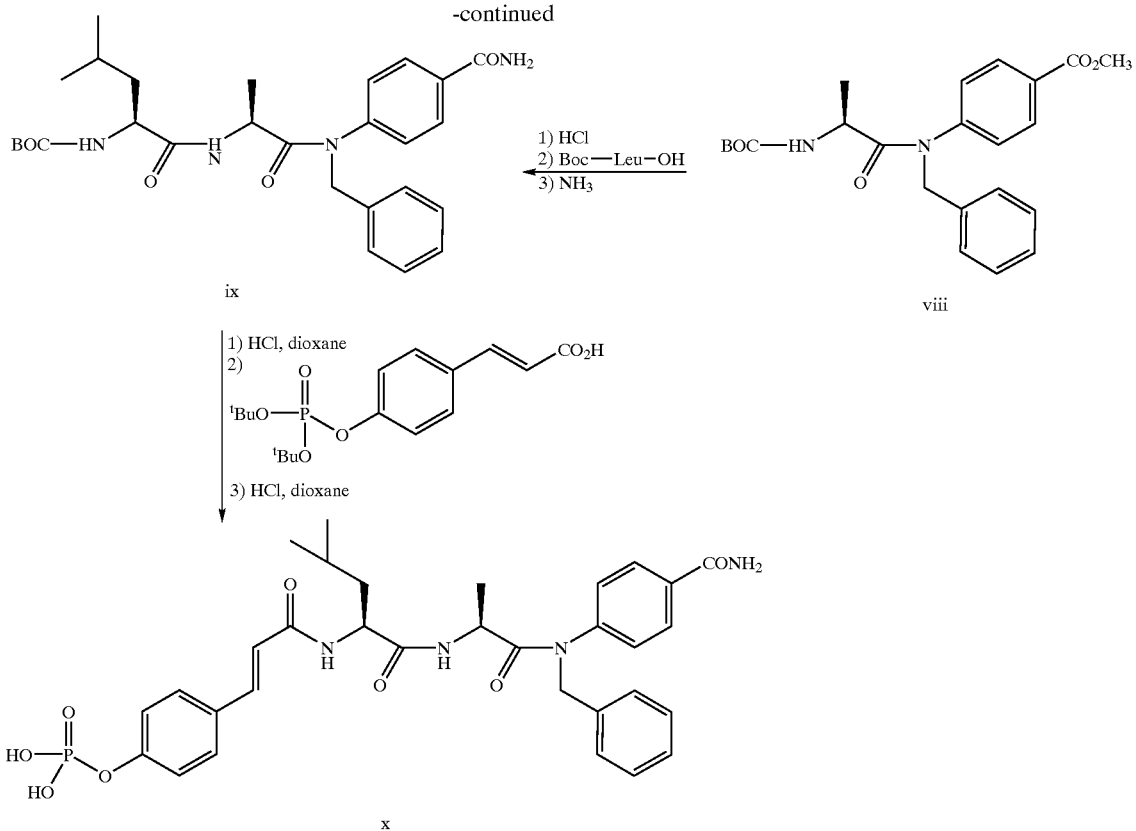

Scheme 2 illustrates a synthesis outline for the preparation of compounds in which $R^1$ is a substituted phenyl and $R^2$ is benzyl (or a substituted benzyl). In this scheme, synthesis begins as outlined in Scheme 1 to provide iii. Conversion of iii to amide viii can be accomplished by treating iii with sodium hydride and benzyl bromide. The remaining steps are essentially the same as those steps described in Scheme 1. Thus, removal of the Boc group in viii, followed by attachment of Boc-leucine and conversion of the methyl ester to an amide (with ammonia) results in formation of ix. Conversion of ix to x follows those steps which were outlined for the conversion of v to vii.

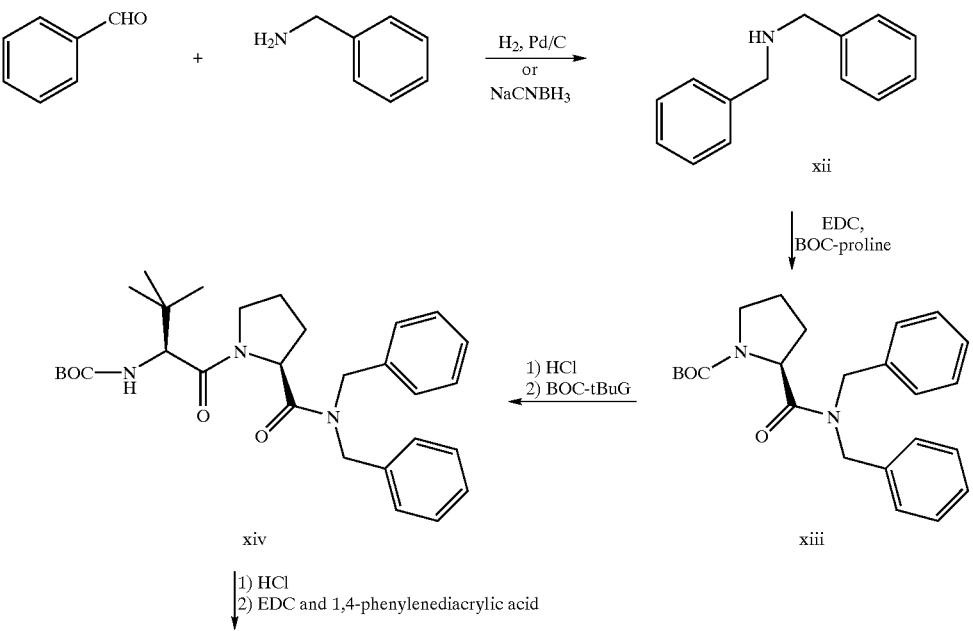

-continued

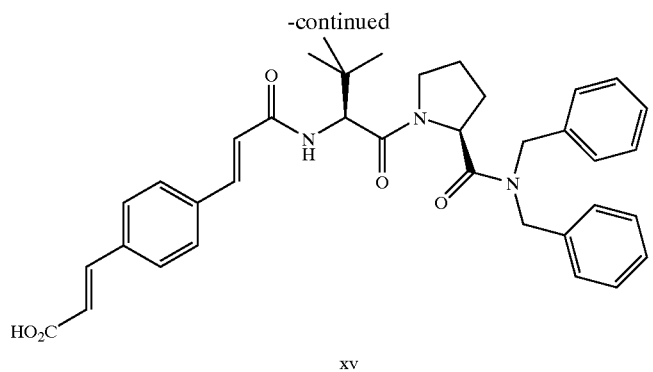

xv

Scheme 3 provides a synthesis outline for compound in which R¹ and R² are each benzyl. One of skill in the art will understand that the method provided will be applicable to other arylalkylamines and substituted arylalkylamiines. As illustrated in Scheme 3, condensation of benzaldehyde and benzylamine, and reduction of the Schiff base initially produced, yields dibenzylamine xii. Acylation of xii with Boc-proline provides xiii, which can be deprotected and acylated with Boc-t-butylglycine to provide xiv. Deprotection of xiv and acylation with 1,4-phenylenediacrylic acid provides the target compound xv.

Substitution patterns on the benzene ring portions of R¹ and R² can be varied by starting the synthesis outlined in Scheme 3 with alternative substituted benzaldehydes and substituted benzylamines. Coupling the resultant dibenzylamine derivative with various amino acids (or alternatively, a dipeptide) and acylation of the N-terminous provides compound of the present invention.

The starting materials used in the synthesis schemes above are generally commercially available or can be prepared using standard synthetic methodology. Scheme 4 provides two reaction schemes for preparing carboxylic acids that effectively add Y—Ar—X—C(O)— to the dipeptides v, ix and xiv (after removal of the Boc protecting group). As can be seen, ethyl 4iodobenzoate (xvi) can be converted to the acid xvii upon treatment with t-butyl acrylate in the presence of palladium catalyst and triphenylphosphine, followed by treatment with HCl to remove the t-butyl ester.

SCHEME 4

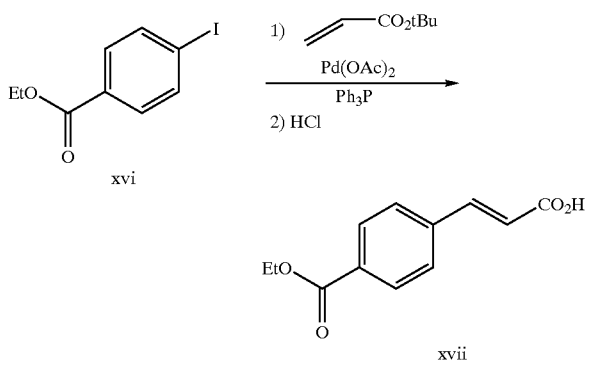

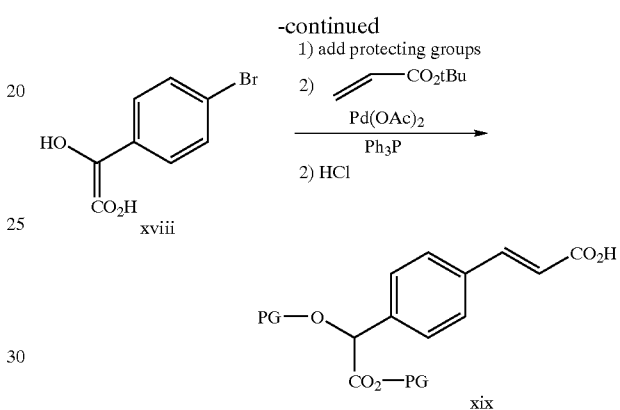

Similarly, 4bromomandelic acid (from Aldrich Chemical Co., St. Louis, Mo., USA, xviii) can be converted to xix by protecting the hydroxy and carboxylic acids groups (with protecting groups generally indicated as PG); coupling an acrylate ester to the aromatic ring (as above) and hydrolyzing the ester with HCl.

Combinatorial and Solid Phase Approaches

Figure 2:
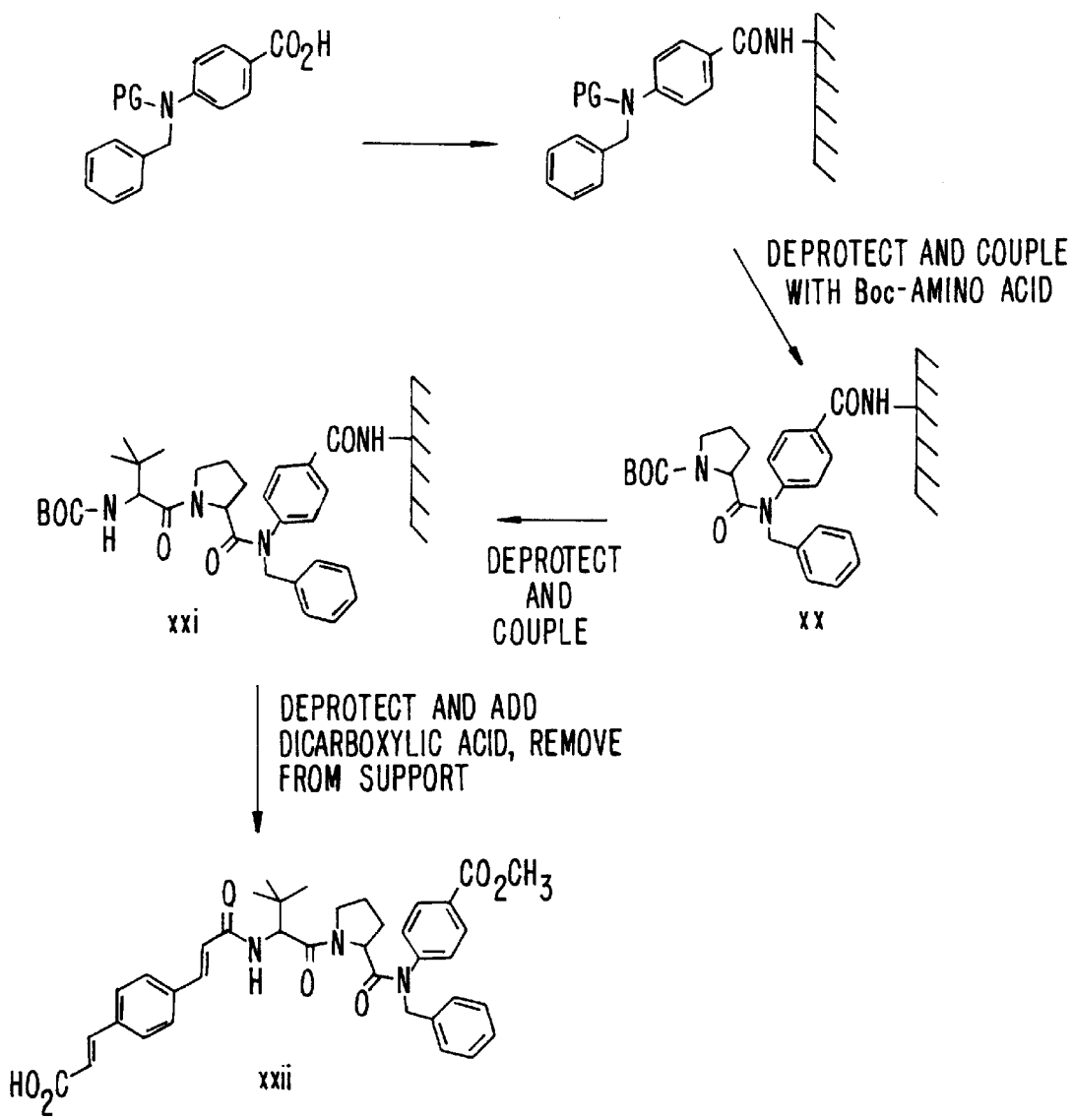
FIG. 2 illustrates the solid-phase synthesis of compounds of the present invention.

Preparation of certain compounds can be accomplished using combinatorial methodology or solid phase synthesis. FIG. 2 illustrates one method for preparing the compounds of the present invention on a resin. Briefly, an appropriately functionalized and protected (with protecting group (PG)) diarylamine can be attached to a solid support. Removal of the protecting group and addition of an amino acid, or mixture of amino acids, results xx. Subsequent removal of the protecting group and addition of a second amino acid, or mixture of amino acids results in the tethered dipeptide xxi. Again, removal of the protecting group and acylation of the free amino group with an acid provides the target compounds xxii. Depending on the nature of the protecting groups, a variety of automated synthesis formats can also be used for preparing the present compounds. A review of the methods (e.g., light directed methods, pin-based methods, flow-channel methods and the like) can be found in U.S. Pat. Nos. 5,556,752 and 5,624,711.

Figure 3:
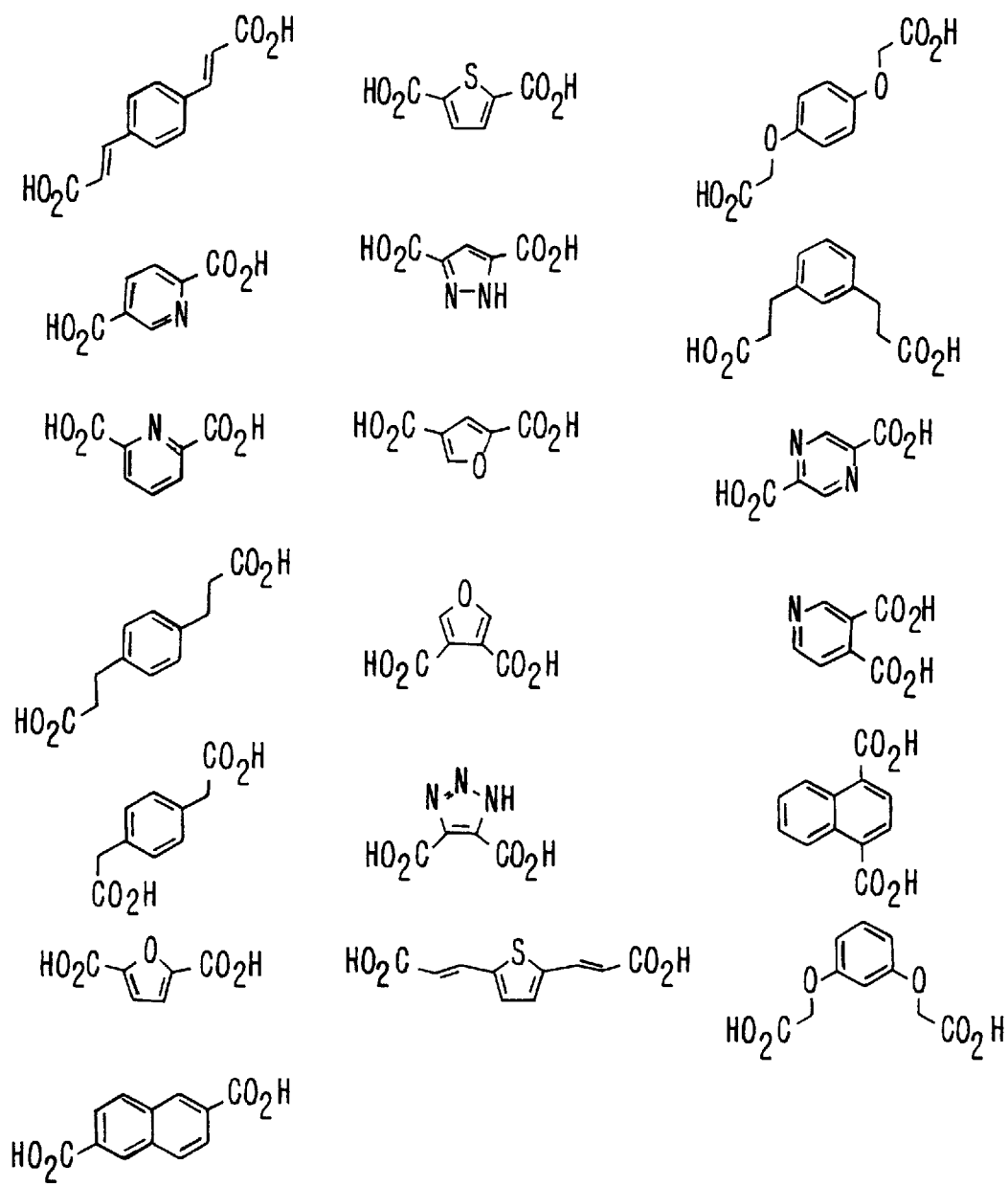
FIG. 3 provides structures for certain dicarboxylic acids that are useful in preparing compounds of formula I.

Other useful methods for preparing the target compounds are those that obviate the need for certain protection and deprotection steps. For example, in FIG. 2, use of a symmetrical aryl dicarboxylic acid makes protection and deprotection of the distal (unreactive site) carboxylic acid unnecessary. Examples of commercially available dicarboxylic acids are provided in FIG. 3.

Analysis of the Compounds

The compounds of the present invention can be evaluated for STAT binding activity using methods such as those described in U.S. Pat. No. 6,207,391 (for STAT6 binding). Other assays for STAT binding can be found in, for example, U.S. Pat. Nos. 5,618,693, 5,639,858 and 5,756,700.

Formulation and Administration of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered topically, including tsansdernally. Accordingly, the present invention also provides pharmaceutical compositions comprising a pharmaceutically acceptable carrier or excipient and either a compound of formula I or a pharmaceutically acceptable salt of a compound of formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. Liquid forms are particularly preferred for topical applications to the eye. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from about 2 mg to about 2000 mg, preferably about 5 mg to about 150 mg according to the particular application and the potency of the active component. The composition can, if desired, also contain other compatible therapeutic agents (e.g., antiviral agents such as acyclovir, ganciclovir, foscarnet and cidofovir).

In therapeutic use as immunomodulators, the compounds utilized in the pharmaceutical method of the invention are administered at the initial dosage of about 0.05 mg/kg to about 20 mg/kg daily. A daily dose range of about 0.05 mg/kg to about 2 mg/kg is preferred, with a daily dose range of about 0.05 mg/kg to about 0.2 mg/kg being most preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The following examples are offered by way of illustration and are not intended to limit the scope of the invention.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses). Electrospray ionization (ESI) mass spectrometry analysis was conducted on a Hewlett-Packard 1100 MSD electrospray mass spectrometer using the HP1100 HPLC for sample delivery. Normally the analyte was dissolved in methanol at 0.1 mg/mL and 1 microliter was infused with the delivery solvent into the mass spectromter which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2mM NH₄OAc in acetonitrile/water as delivery solvent.

Example 1

This example illustrates the synthesis of compound 1.

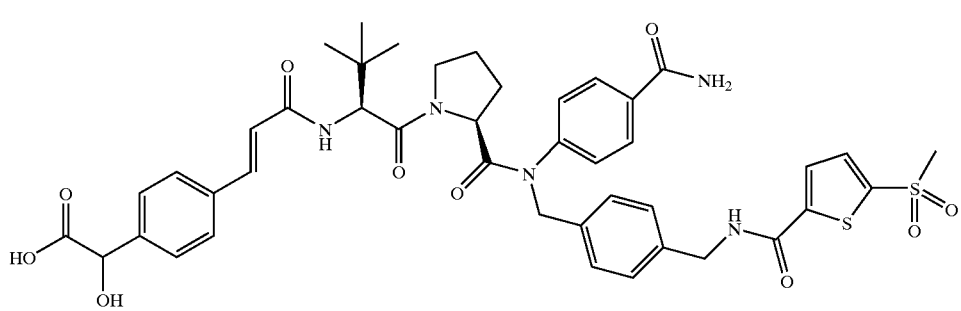

1

1.1 Preparation of Compound 1.1

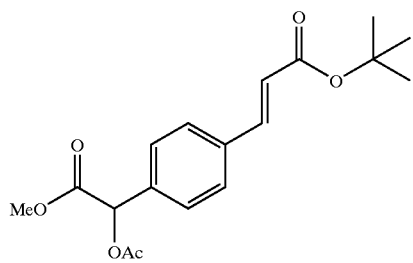

1.1

To 4-bromomandelic acid (10.0 g, 43.3 mmol) in benzene/methanol (9:1, 200 mL) at 0° C. was added dropwise (triethylsilyl)diazomethane (2.0 M in hexanes, 22 mL, 44 mmol). After 20 minutes, the solution was concentrated in vacuo to afford a colorless oil which was used without further purification.

To a solution of the crude methyl ester in acetic anhydride (100 mL) was added NaOAc (5.0 g, 61 mmol). The resulting solution was stirred for 3 hours, diluted with H₂O, and stirred for an additional 48 h. The reaction mixture was diluted with CH₂Cl₂, the two layers were separated, and the organic layer was washed with H₂O (3×). The organic layer was dried over MgSO₄, filtered, and concentrated in vacuo to afford a thick oil. Trituration of the oil with toluene (2×) provided 9.0 g of a white solid.

To a solution of the white solid (9.0 g) and t-butyl acrylate (13.7 mL, 93 mmol) in Et₃N (60 mL) and toluene (5 mL) was added Pd(OAc)₂ (0.7 g, 3.1 mmol) and triotolylphosphine (1.0 g, 3.2 mmol). The solution was heated to reflux and stirred for 3 h. The reaction was cooled, filtered through celite, concentrated in vacuo, and purified by flash chromatography to yield 9.0 g (62% over three steps) of 1.1.

1.2 Preparation of Compound 1.2

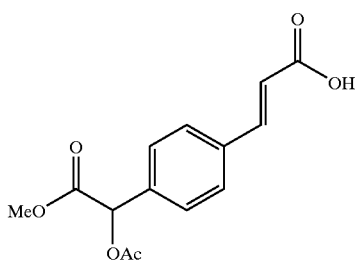

1.2

To a solution of 1.1 (9.0 g, 26.5 mmol) in CH₂Cl₂ (60 mL) at 0° C. was added TFA (40 mL) dropwise over 15 minutes. The resulting solution was warmed to rt and stirred for 1.5 h. The reaction was concentrated in vacuo and triturated with CH₂Cl₂ (4×). The residue was dissolved in CH₂Cl₂ (50 mL) and hexanes (700 mL) was added dropwise resulting in the precipitation of a white solid. Collection of the white solid by filtration yielded 6.0 g (81%) of 1.2.

1.3 Preparation of Compound 1.3

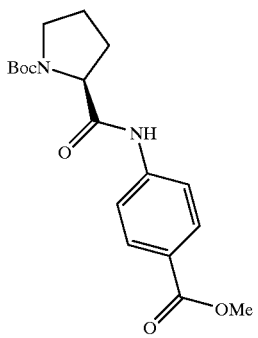

1.3

Methyl 4-aminobenzoate (9.1 g, 60 mmol) and Boc-L-proline (15 g, 70 mmol) were dissolved in CH₂Cl₂. To this solution was added NMM (33 mL, 300 mmol) and EDC (19.2 g, 100 mmol). After 16 h, the reaction was quenched with 10% aqueous citric acid. The aqueous layer was extracted with CH₂Cl₂ (3×); the organic layer was extracted with saturated NaHCO$_3$ (2×), dried over MgSO$_4$, and concentrated in vacuo to afford 19 g of a yellow oil. Purification by silica gel chromatography provided 16 g (76%) of 1.3 as a pale yellow foam.

1.4 Preparation of Compound 1.4

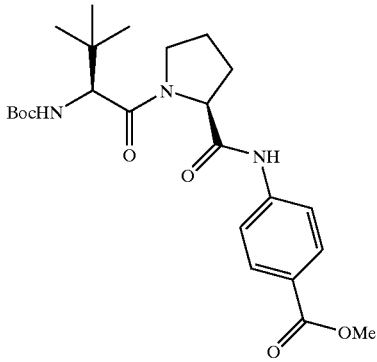

1.4

To ester 1.3 (8 g, 23 mmol) in EtOAc (150 mL) was added HCl (4 M in dioxane, 50 mL, 200 mmol). After 45 minutes, the reaction was concentrated in vacuo. The residue was triturated with CH$_2$Cl$_2$ and the HCl salt produced was used without further purification.

The HCl salt was dissolved in CH$_2$Cl$_2$ (100 mL) and to this solution was added Boc-L-t-butyl glycine (5.3 g, 27.6 mmol) and NMM (12.6 mL, 27.6 mmol). Five minutes later EDC (4.4 g, 27.6 mmol) and HOBT (3.1 g, 27.6 mmol) were added. The reaction was stirred for 8 h and then quenched with 10% aqueous citric acid. The aqueous layer was extracted with CH$_2$Cl$_2$ (2×). The combined organic portions were washed with saturated NaHCO$_3$, dried over MgSO$_4$, and concentrated in vacuo to provide 10 g of a yellow oil that was purified by filtering through silica gel to yield 6 g (57%) of 1.4 as a yellow foam.

1.5 Preparation of Compound 1.5

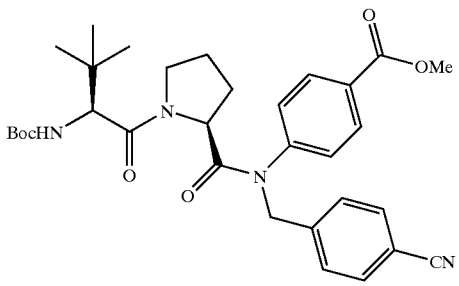

1.5

To a 0° C. solution of ester 1.4 (4.61 g, 10.0 mmol) and α-bromo-p-tolunitrile in CH$_2$Cl$_2$/DMF (1:1, 100 mL) was added NaH (60% dispersion in mineral oil, 433 mg, 10.8 mmol). The reaction was warmed to rt and stirred for 1.5 h. The mixture was concentrated in vacuo and the residue was partitioned between CH$_2$Cl$_2$ and aqueous NH$_4$Cl. The aqueous layer was extracted with CH$_2$Cl$_2$ (2×). The combined organic layer was dried over MgSO$_4$ and concentrated in vacuo to provide 5 g of a yellow oil. Purification by silica gel chromatography afforded 3.16 g (55%) of 1.5 as a white foam.

1.6 Preparation of Compound 1.6

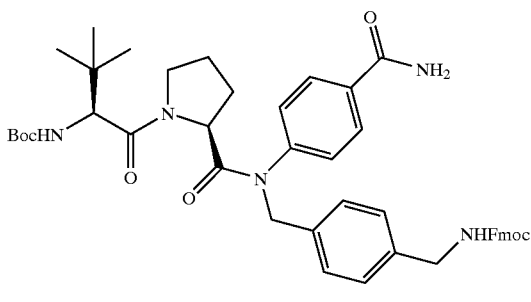

1.6

To ester 1.5 (600 mg, 1.0 mmol) in methanol (2 mL) was added ammonia (40 mL). The reaction mixture was transferred to a sealed tube and heated at 55° C. for 3 d. The solution was cooled and concentrated in vacuo to provide a yellow oil. This aminolysis reaction was repeated using 1.5 g of X; the products from these two reactions were combined to afford 2 g of the primary amide which was used in the next reaction without further purification.

The crude amide was dissolved in EtOH (80 mL) and ammonia was bubbled through the solution for 5 minutes. To this solution was added a catalytic amount of Raney nickel (50% slurry in H$_2$O). The reaction mixture was placed under a hydrogen atmosphere (50 psi) for 3 h, filtered through celite, and concentrated in vacuo to provide 2 g of the amine which was used without further purification.

To the crude amine in dioxane (60 mL) and H$_2$O (20 mL) at 0° C. was added NaHCO$_3$ (2.96 g, 35.3 mmol). Fmoc-Cl (1.09 g, 4.24 mmol) was added and stirring was continued for 1 h. The reaction was quenched with 1 M HCl and the aqueous layer was extracted with CH$_2$Cl$_2$ (3×). The organic layer was dried over MgSO$_4$, concentrated in vacuo, and purified by silica gel chromatography to afford 2.2 g (77% over three steps) of 1.6 as a white solid.

1.7 Preparation of Compound 1.7

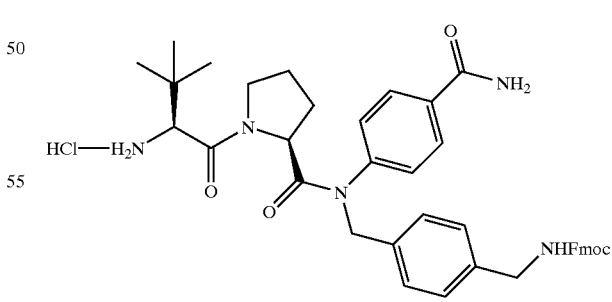

1.7

To a solution of 1.6 (2.2 g, 2.8 mmol) in EtOAc (12 mL) was added HCl (4.0 M in dioxane, 12 mL). After 30 min, the reaction mixture was concentrated in vacuo and then triturated with CH$_2$Cl$_2$ (3×) to afford 2.1 g of 1.7 as a white solid which was used without further purification.

1.8 Preparation of Compound 1.8

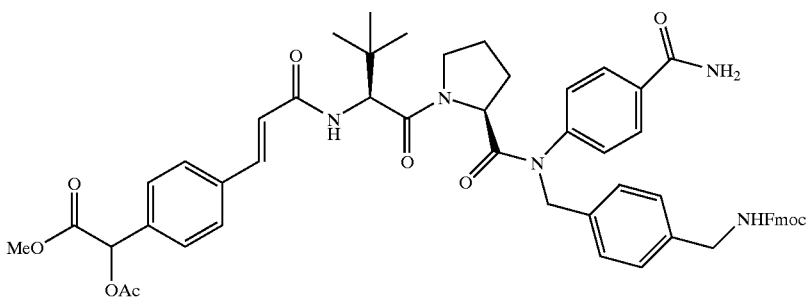

1.8

To a portion of 1.7 (500 mg, 0.69 mmol) in CH$_2$Cl$_2$ (5 mL) was added 1.2 (383 mg, 1.38 mmol) and NMM (0.23 mL, 2.07 mmol). After stirring for 10 min, EDC (265 mg, 1.38 mmol) and HOBT (211 mg, 1.38 mmol) were added to the reaction mixture. The reaction was stirred for 10 h and then quenched with 10% aqueous citric acid. The aqueous layer was extracted with CH$_2$Cl$_2$. The organic layer was washed with saturated NaHCO$_3$, dried over MgSO$_4$, and concentrated in vacuo to afford 650 mg of a colorless oil. Purification by silica gel chromatography provided 500 mg (77%) of 1.8 as a white solid.

1.9 Preparation of Compound 1.9

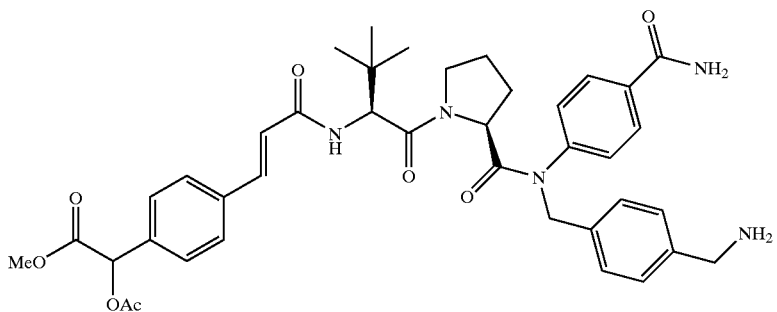

1.9

Ester 1.8 (500 mg, 0.53 mmol) was stirred in CH$_2$Cl$_2$ (20 mL) and Et$_2$NH (5 mL) for 12 h. The reaction mixture was concentrated in vacuo and triturated with CH$_2$Cl$_2$ (3×). The solid was redissolved in CH$_2$Cl$_2$ (3 mL) and diluted with hexanes (25 mL). The resulting precipitate was removed by filtration and the filtrate was concentrated in vacuo to yield 440 mg of 1.9 which was used without further purification.

1.10 Preparation of Compound 1.10

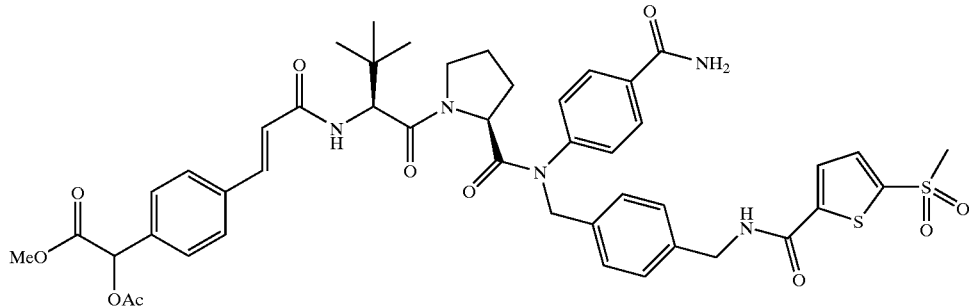

1.10

A portion of 1.9 (50 mg, 0.07 mmol) was dissolved in CH$_2$Cl$_2$ (1 mL) and a few drops of DMF. To this solution was added 5-methanesulfonyl-2-thiophenecarboxylic acid (29 mg, 0.14 mmol), EDC (27 mg, 0.14 mmol), and NMM (50 μL, 0.54 mmol). After stirring for 12 h, the reaction mixture was concentrated in vacuo and the crude material purified by flash chromatography to yield 17 mg (27%) of 1.10 as a white solid.

1.11 Preparation of Compound 1

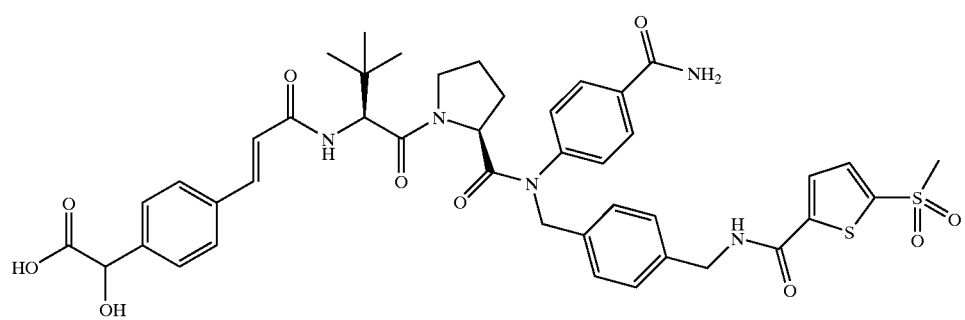

To ester 1.10 (17 mg, 0.019 mmol) in THF/MeOH/H$_2$O (2:2:1, 5 mL) was added LiOH (6 mg, 0.25 mmol). After 30 minutes, the reaction was quenched with 8 drops of acetic acid and the solution was concentrated in vacuo. Purification of the crude material by RP-HPLC afforded 12 mg (74%) of 1 as a white solid. ESI(−) 856.2, 857.2, 858.2, 859.2, 860.2.

Example 2

This example illustrates the synthesis of compound 2.

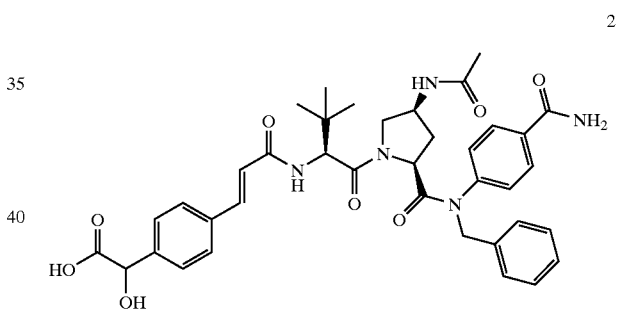

2.1 Preparation of Compound 2.1

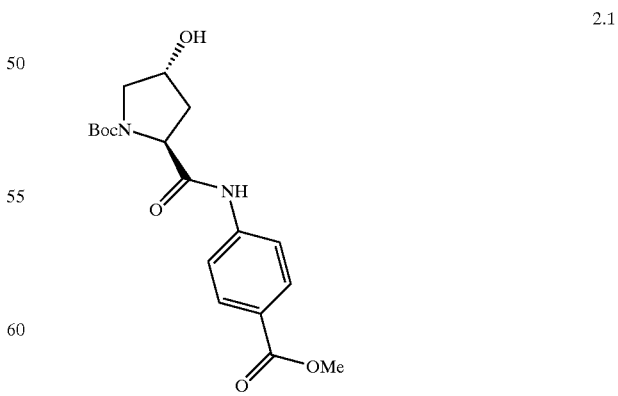

To a solution of Boc-trans-4-hydroxy-L-proline (2.5 g, 10.8 mmol) in DMF (15 mL) was added methyl 4-aminobenzoate (1.2 g, 8.3 mmol), NMM (1 mL, 10.8 mmol), HBTU (4.2 g, 11 mmol), and HOBT (1.6 g, 11 mmol). The reaction was stirred overnight and the reaction mixture was concentrated in vacuo. The residue was dissolved in EtOAc (150 mL) and the organic layer was washed with 10% aqueous citric acid and 1 N NaHCO$_3$. The organic layer was dried over MgSO$_4$, filtered, and concentrated in vacuo. The residue was purified by silica gel chromatography to afford 2.1 g (71 %) of 2.1.

2.2 Preparation of Compound 2.2

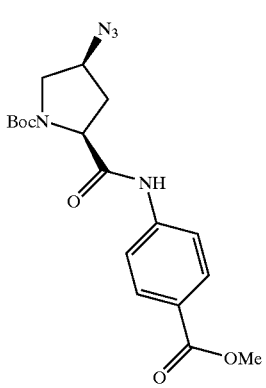

2.2

To a solution of alcohol 2.1 (1.8 g, 4.9 mmol) in DMF (4 mL) was added methanesulfonyl chloride (0.45 mL, 5.9 mmol) and Et$_3$N (0.59 mL, 5.9 mmol). The solution was stirred at rt for 5 h, concentrated in vacuo, and used without further purification.

The crude mesylate was dissolved in DMF (20 mL) and sodium azide (0.9 g, 14 mmol) was added. The reaction mixture was warmed to 65° C. and stirred for 24 h. DMF was removed in vacuo and the resulting residue was dissolved EtOAc. The organic layer was washed with H$_2$O and brine, dried over MgSO$_4$, concentrated in vacuo, and purified by silica gel chromatography to provide 1.37 g (72%) of 2.2.

2.3 Preparation of Compound 2.3

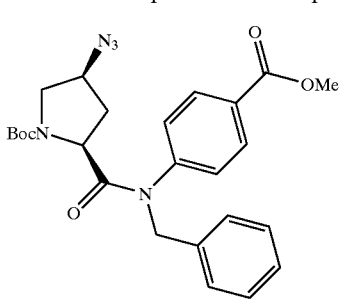

2.3

Amide 2.2 (1.3 g, 3.3 mmol) and benzyl bromide (0.47 ML, 3.7 mmol) were dissolved in DMF (10 mL) and CH$_2$Cl$_2$ (10 mL). The solution was cooled to 0° C. and NaH (60% dispersion in mineral oil, 0.15 g, 3.63 mmol) was added portionwise. The solution was slowly warmed to rt and allowed to stir for 24 h. The reaction was quenched with 10% aqueous citric acid, the solution was concentrated in vacuo, and the resulting residue was dissolved in EtOAc. The organic layer was washed with H$_2$O and brine, dried over MgSO$_4$, and concentrated in vacuo. Purification by silica gel chromatography provided 1.23 g (78%) of 2.3.

2.4 Preparation of Compound 2.4

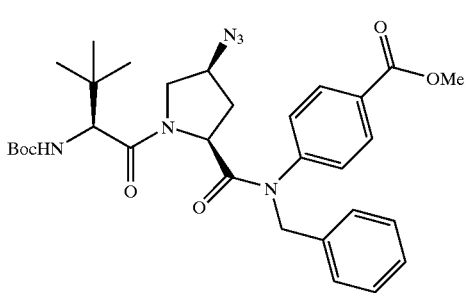

2.4

Ester 2.3 (1.23 g, 2.57 mmol) was stirred in HCl (4N in dioxane, 20 mL, 80 mmol) for 30 minutes. The reaction mixture was concentrated in vacuo to afford the amine HCl salt which was used in the next reaction without further purification.

The crude material was dissolved in CH$_2$Cl$_2$ (10 mL). To this solution was added Boc-L-t-butylglycine (0.80 g, 3.45 mmol), EDC (0.90 g, 4.6 mmol), HOBT (0.7 g, 4.6 mmol), and NMM (0.47 mL, 4.6 mmol). After stirring overnight, the reaction mixture was concentrated in vacuo. The residue was dissolved in EtOAc and washed with 10% aqueous citric acid, 1 N NaHCO$_3$, and dried over MgSO$_4$. The resulting solution was concentrated in vacuo and purified by silica gel chromatography to yield 1.0 g (66%) of 2.4 as a white solid.

2.5 Preparation of Compound 2.5

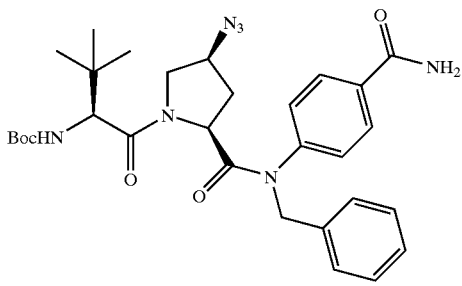

2.5

Ester 2.4 (1.0 g, 1.7 mmol) was dissolved in a saturated solution of ammonia in methanol (25 mL) and stirred in a sealed tube for 42 h. The reaction was concentrated in vacuo and the residue purified by silica gel chromatography to afford 0.7 g (72%) of 2.5.

2.6 Preparation of Compound 2.6

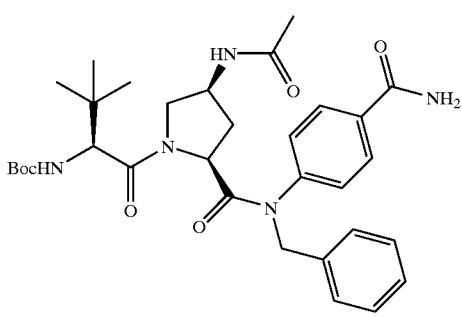

2.6

To a solution of azide 2.5 (0.2 g, 0.36 mmol) in methanol (10 mL) was added 10% Pd/C (0.036 mmol). The flask was equipped with a balloon of H$_2$ and the reaction was stirred for 1 h. The solution was filtered through celite, concentrated in vacuo, and the material was used without further purification.

The residue was dissolved in DMF (5 mL). To this solution was added acetic anhydride (40 μL, 0.43 mmol) and NMM (0.1 mL, 1.0 mmol). After the reaction mixture was stirred for 24 h, the solvent was removed in vacuo, and the residue was dissolved in EtOAc. The organic solution was extracted with 10% aqueous citric acid and 1 N NaHCO₃, dried over MgSO₄, filtered, and concentrated in vacuo. Purification by silica gel chromatography provided 73 mg (36%) of 2.6.

2.7 Preparation of Compound 2.7

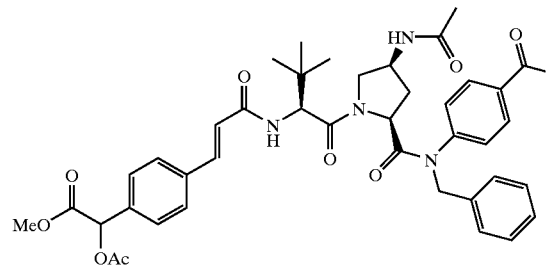

2.7

Amide 2.6 (180 mg, 0.35 mmol) was stirred in HCl (4N in dioxane, 3 mL, 12 mmol) for 30 minutes. The reaction mixture was concentrated in vacuo to afford the HCl salt which was used in the next reaction without further purification.

The crude material was dissolved in DMF (6 mL). To this solution was added carboxylic acid 1.2 (0.1 g, 0.35 mmol), EDC (0.13 g, 0.7 mmol), HOBT (0.11 g, 0.7 mmol), and NMM (0.28 mL, 2.8 mmol). After stirring overnight, the solvent was removed in vacuo. The residue was dissolved in EtOAc and the organic layer was washed with 10% aqueous citric acid and 1 N NaHCO₃. The organic layer was dried over MgSO₄, filtered, and concentrated in vacuo. Purification by silica gel chromatography provided 163 mg (62%) of 2.7.

2.8 Preparation of Compound 2

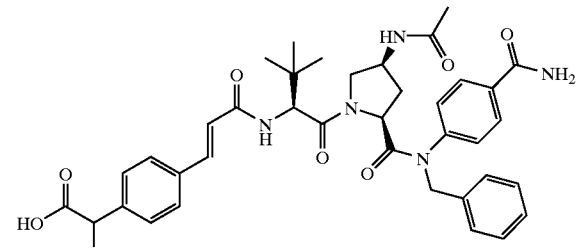

2

To a solution of 2.7 (50 mg, 0.07 mmol) in MeOH (2 mL) was added 1 N NaOH (2 mL, 2 mmol). The reaction was stirred for 15 minutes, neutralized with concentrated HCl, and extracted with EtOAc. The organic layer was dried over MgSO₄ and concentrated in vacuo. Purification by RP-HPLC provided 10 mg (22%) of 2 as a white solid. ESI(+) 698.3.

Example 3

This example illustrates the preparation of compound 3.

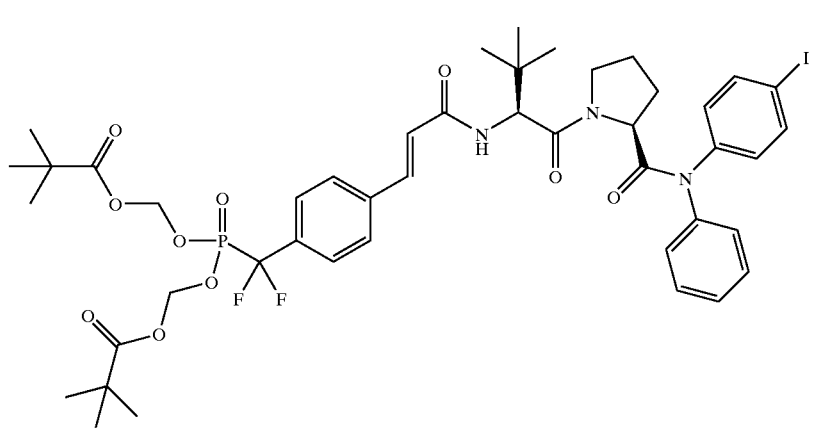

3

3.1 Preparation of Compound 3.1

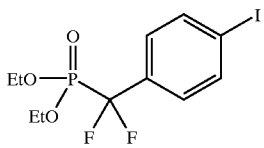

3.1

T a suspension of 4iodobenzoyl chloride (9.86 g, 37 mmol) in triethylphosphite (8.2 mL, 47.9 mmol) was added toluene (50 mL). The reaction mixture was heated to reflux for 30 minutes, cooled to rt, and then concentrated in vacuo.

The residue was cooled to 0° C. and diethylaminosulfur trifluoride (20 mL, 152 mmol) was added portionwise. The reaction was stirred at 0° C. for 3 h, diluted with $CH_2Cl_2$, and then quenched with saturated aqueous $NaHCO_3$ at 0° C. The aqueous layer was washed with $CH_2Cl_2$, EtOAc, and hexanes. The combined organic portions were dried over $MgSO_4$, concentrated in vacuo and purified by silica gel chromatography to provide 2.3 g (16%) of 3.1.

3.2 Preparation of Compound 3.2

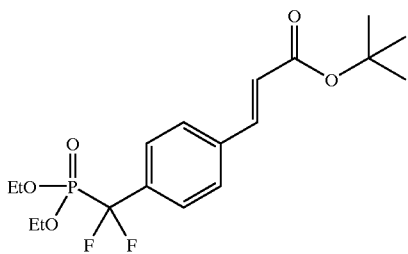

3.2

To a solution of the iodide 3.1 (1.37 g, 3.5 mmol) in $Et_3N$ (15 mL) was added t-butyl acrylate (1.02 mL, 6.9 mmol), $Pd(OAc)_2$ (79 mg, 0.35 mmol, and tri-o-tolylphosphine (106 mg, 0.35 mmol). The reaction mixture was heated to 60° C. for 2 h at which time starting material still remained. Additional t-butyl acrylate (1.02 mL, 6.9 mmol) and $Pd(OAc)_2$ (35 mg, 0.17 mmol) were added and the reaction mixture was stirred for 3 h. The solution was cooled to rt, filtered through celite, and concentrated in vacuo. Silica gel chromatography provided 1.15 g (84%) of 3.2 as an orange oil.

3.3 Preparation of Compound 3.3

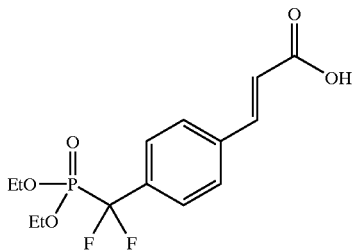

3.3

Ester 3.2 (1.5 g, 3.84 mmol) was dissolved in $CH_2Cl_2$/TFA (1:1, 20 mL). After 1 h, the solution was concentrated in vacuo and the residue was used without further purification.

3.4 Preparation of Compound 3.4

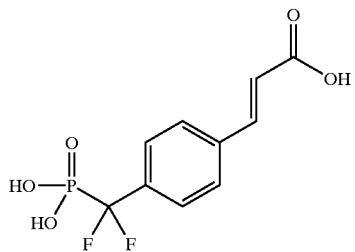

3.4

To the acid 3.3 (178 mg, 0.53 mmol) in $CH_2Cl_2$ (5 mL) was added bis(trimethylsilyl)trifluoroacetamide (0.14 mL, 0.53 mmol). After 30 minutes, the reaction was cooled to 0° C. and iodotrimethylsilane (0.30 mL, 2.1 mmol) was added. The reaction was stirred at 0° C. for 30 min and then at rt for 30 min. The solution was concentrated in vacuo. The residue was dissolved in $CH_3CN/H_2O$/TFA (10:5:3, 9 mL), stirred an additional 30 minutes, concentrated in vacuo, and used without further purification.

3.5 Preparation of Compound 3.5

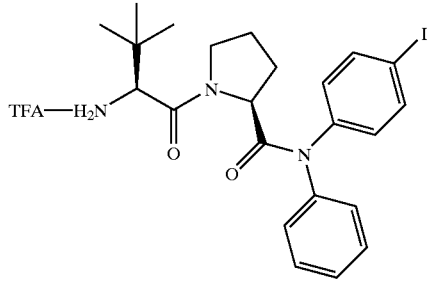

3.5

To a solution of Boc-L-proline (2.3 g, 10.7 mmol) in $CH_2Cl_2$ (50 mL) was added 4-iodoaniline (2.3 g, 10.5 mmol) and EDC (2.1 g, 11.0 mmol). After 4 h, the reaction was quenched with 1 N HCl. The organic layer was washed with 1 N NaOH, dried over $MgSO_4$, and concentrated in vacuo to provide 4.4 g of a foam which was used without further purification.

The foam was dissolved in $CH_2Cl_2$ and to this solution was added triphenylbismuth (7.0 g, 15.9 mmol), $Cu(OAc)_2$ (2.9 g, 15.9 mmol) and $Et_3N$ (3 mL, 21.6 mmol). The reaction was stirred vigorously overnight, filtered through celite, and the filtrate was concentrated in vacuo. Partial purification by flash chromatography afforded 4.4 g of a diphenylamnide foam which was used in the next reaction without additional purification.

The diphenyl amide was dissolved in $CH_2Cl_2$/TFA (1:1, 40 mL) and stirred 30 minutes. The solvents were removed in vacuo to provide 3.1 g of the TFA salt which was used in the next reaction without further purification.

The amine TFA salt was dissolved in $CH_2Cl_2$ (20 mL) and to this solution was added Boc-L-t-butylglycine (2.2 g, 9.5 mmol), EDC (1.8 g, 9.5 mmol), and $Et_3N$ (1.3 mL, 17.7 mmol). After 6 h, the reaction was quenched with 1 N HCl; the organic layer was washed with 1 N NaOH and brine, dried over $MgSO_4$, and concentrated in vacuo. The material was purified by silica gel chromatography.

The Boc group was removed by dissolving the material in $CH_2Cl_2$/TFA (1:1, 10 mL). After 30 minutes, the solvents were removed in vacuo. The residue was dissolved in $CH_2Cl_2$; the organic layer was extracted with 1 N NaOH, dried over $MgSO_4$, and concentrated in vacuo to provide 0.53 g (8% over 5 steps) of 3.5.

3.6 Preparation of Compound 3.6

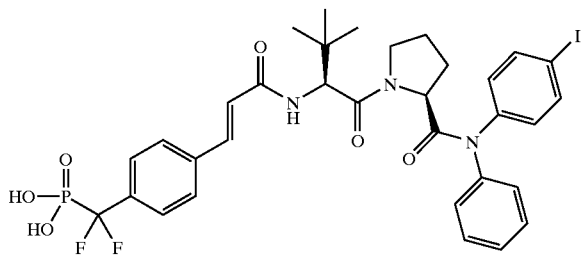

Phosphonate 3.4 (29 mg, 0.1 mmol) and amine—TFA salt 3.5 (35 mg, 0.07 mmol) were dissolved in DMF (2 mL). To this solution was added HOBT (15 mg, 0.1 mmol), N,N-diisopropylethylamine (49 μL, 0.28 mmol), and HBTU (38 mg, 0.1 mmol). After stirring overnight, the reaction was quenched with 0.5 M HCl (10 mL) resulting in precipitate formation. The mixture was placed in a refrigerator for 2 h and then filtered to provide 28 mg of a tan solid. Purification by RP-HPLC afforded 5.8 mg (11%) of 3.6 as a white solid. ESI(−) 765.5.

3.7 Preparation of Compound 3

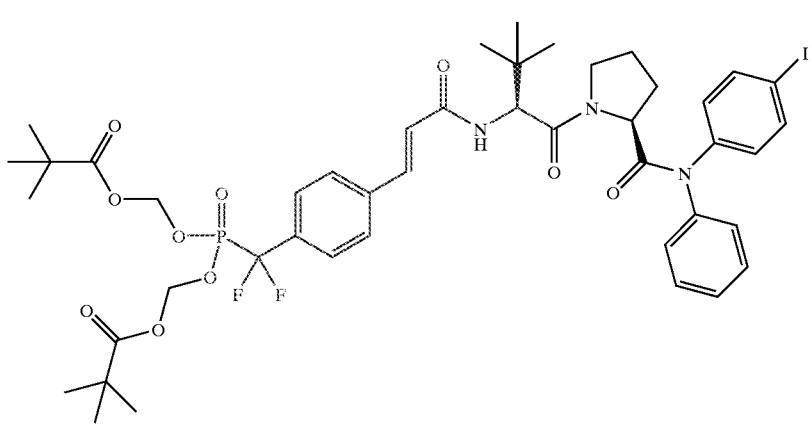

To a suspension of phosphonate 3.6 (150 mg, 0.2 mmol) in $H_2O$ was added NaOH (18 mg, 0.45 mmol). To this slightly cloudy solution was added $AgNO_3$ (68 mg, 0.42 mmol). The round-bottom flask was wrapped in foil and transferred to a refrigerator. After 3 h, the solution was filtered, the solid was suspended in dry toluene (3 mL), and iodomethyl pivalate (145 mg, 0.6 mmol) was added. After stirring overnight, solvent was removed in vacuo and the residue was purified by silica gel chromatography to afford 3 as an off-white foam. ESI(+) 994.2

Example 4

Using methods similar to those described in Examples 1 and 2, the compounds provided in Table 1 were prepared and evaluated as inhibitors of STAT6 binding (duplex formation). The assay is described in U.S. Pat. No. 6,207,391, filed Mar. 31, 1998. In each of the tables below: a + symbol indicates and IC50 of >100 μM; a ++ symbol indicates and $IC_{50}$ of 50–100 μM; a +++ symbol indicates and $IC_{50}$ of 1–50 μM; and a ++++ symbol indicates and $IC_{50}$ of <1.0 μM.

TABLE 1

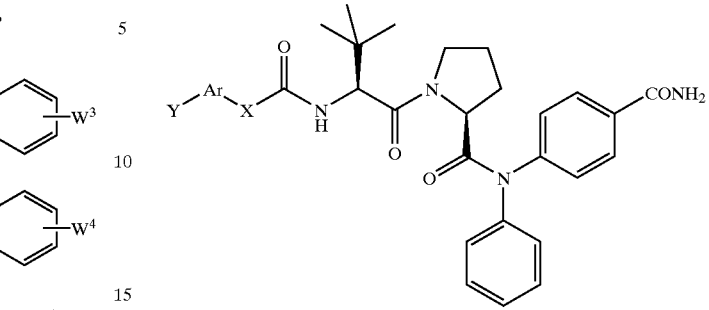

| —W$^{1a}$ | —W$^{1b}$ | —W$^{3}$ | —W$^{4}$ | IC50 |
|---|---|---|---|---|
| —NHAC | H | 4-CONH$_2$ | H | +++ |
| H | H | 4-CONHPh | H | + |
| H | —NH$_2$ | 4-CONH$_2$ | H | +++ |
| H | —NH-Tosyl | 4-CONH$_2$ | H | + |
| H | —NHAc | 4-CONH$_2$ | H | +++ |
| H | —NHBz | 4-CONH$_2$ | H | +++ |
| H | H | 4-CONH$_2$ | 4-CH$_2$NH$_2$ | +++ |
| H | —NHCOCH(CH$_3$)$_2$ | 4-CONH$_2$ | H | +++ |
| H | —N(CH$_3$)$_2$ | 4-CONH$_2$ | H | ++ |
| H | —NHCO$_2$Bn | 4-CONH$_2$ | H | +++ |
| H | —N(Bn)$_2$ | 4-CONH$_2$ | H | + |
| H | —NHSO$_2$CH$_3$ | 4-CONH$_2$ | H | +++ |

Example 5

Compounds having the formulae provided in Table 2 were prepared using methodology similar to that provided in the Examples above.

TABLE 2

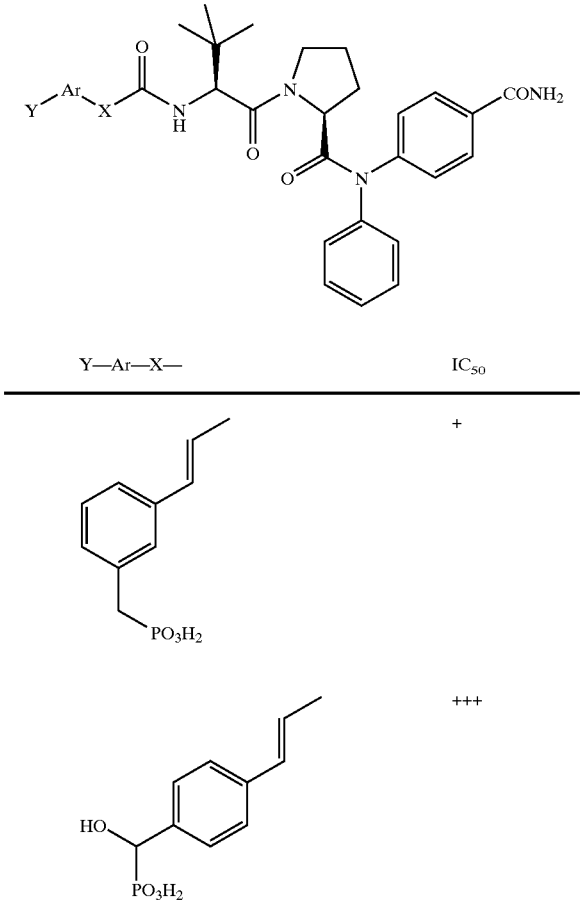

TABLE 2-continued
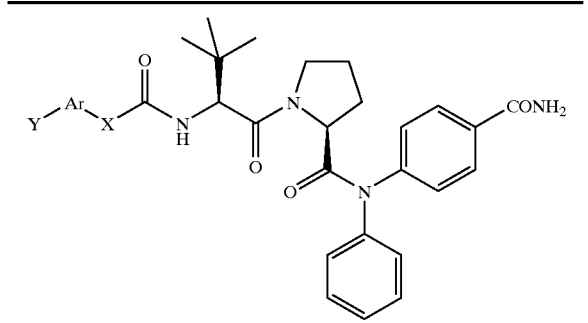
| Y—Ar—X— | IC$_{50}$ |
|---|---|
| 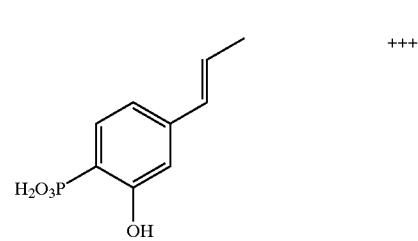 | +++ |
| 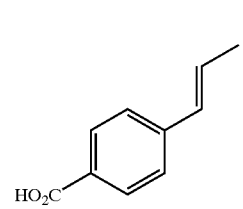 | +++ |
| 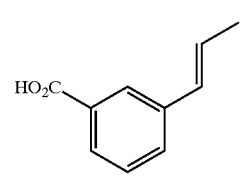 | + |
| 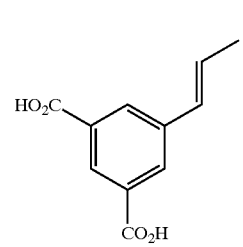 | + |
TABLE 2-continued
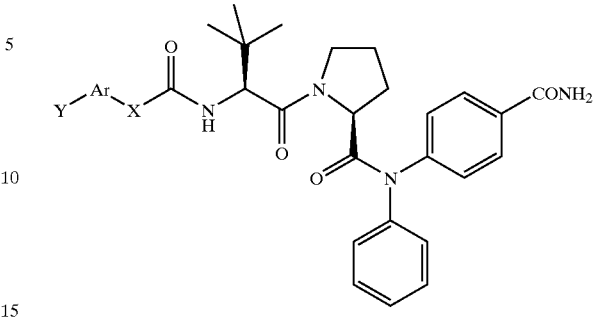
| Y—Ar—X— | IC$_{50}$ |
|---|---|
| 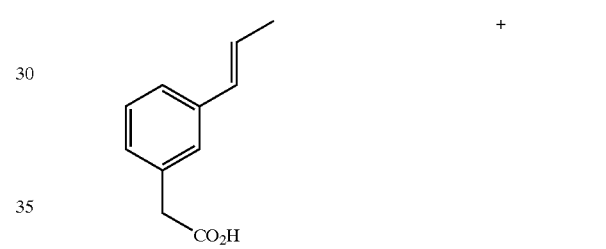 | +++ |
| 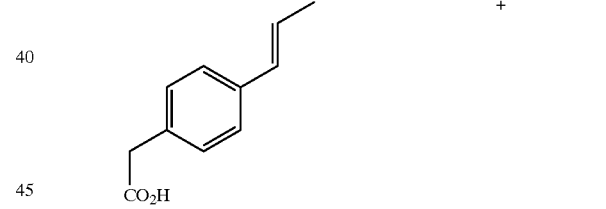 | + |
| 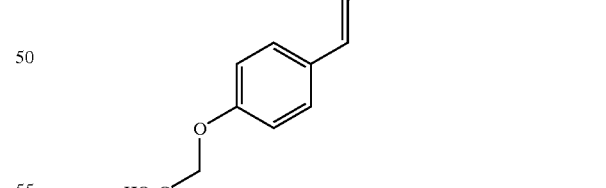 | + |
| 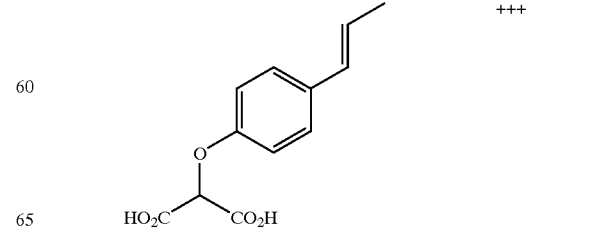 | + |

TABLE 2-continued

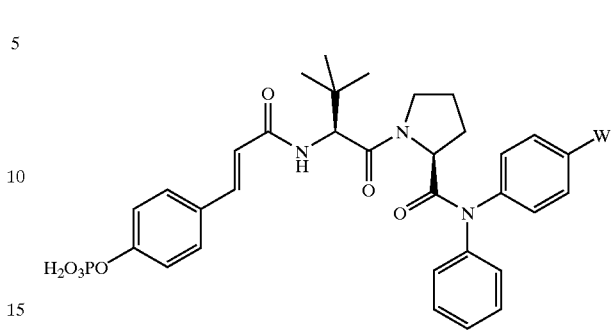

| Y—Ar—X— | IC$_{50}$ |
|---|---|
| (4-propenylphenyl)-CH$_2$-CH(CO$_2$H)- with HO$_2$C | +++ |
| (4-propenylphenoxy)-CF(CO$_2$H)- with HO$_2$C | +++ |
| 5-propenyl-pyridine-3-CO$_2$H | + |
| 6-propenyl-pyridine-3-CO$_2$H | + |
| 6-propenyl-pyridine-2-CO$_2$H | + |

Example 6

The compounds shown in Tables 3, 4 and 5 were prepared using steps similar to those described in the examples above. In many instances the starting materials were different and certain additional steps involving reductions and/or acylations were used.

TABLE 3

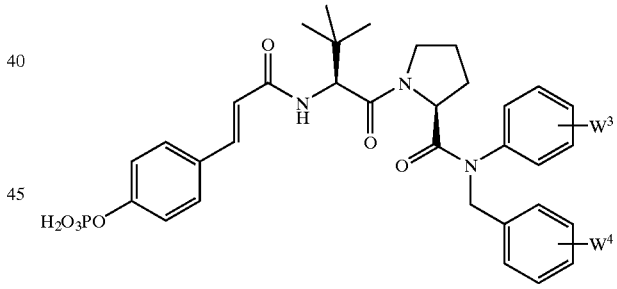

| —W | IC$_{50}$ |
|---|---|
| H | ++++ |
| CH$_3$ | ++++ |
| Cl | ++++ |
| I | ++++ |
| CONH$_2$ | ++++ |
| CO$_2$CH$_3$ | ++++ |
| CO$_2$H | +++ |
| OCH$_3$ | ++++ |
| OH | ++++ |

TABLE 4

[structure with W$^3$ on anilide phenyl and W$^4$ on benzyl group; H$_2$O$_3$PO-phenyl-CH=CH-CO-NH-C(tBu)H-CO-pyrrolidine-CO-N(aryl)(benzyl)]

| —W$^3$ | —W$^4$ | IC$_{50}$ |
|---|---|---|
| H | H | ++++ |
| CONH$_2$ | H | ++++ |
| CON(CH$_3$)$_2$ | H | ++++ |
| H | 4-phenyl | +++ |
| H | 4-t-butyl | +++ |
| H | 4-I | ++++ |
| 4-CONH$_2$ | 4-CH$_2$NHAc | ++++ |
| 4-CH$_2$NHAc | 4-CONH$_2$ | ++++ |
| 4-CONH$_2$ | 4-CH$_2$NH$_2$ | ++++ |
| 3-CONH$_2$ | 4-CH$_2$NHAc | ++++ |
| 3-CH$_2$NHAc | 4-CONH$_2$ | ++++ |

TABLE 5

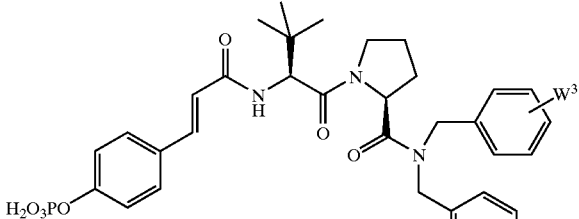

| —W³ | —W⁴ | IC₅₀ |
| --- | --- | --- |
| H | H | ++++ |
| 4-CONH₂ | 4-CN | ++++ |
| 4-CONH₂ | 3-CH₂NHAc | ++++ |
| 4-CONH₂ | 4-CH₂NHAc | ++++ |
| 3-CONH₂ | 3-CH₂NHAc | +++ |
| 4-CONH₂ | H | ++++ |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of the formula:

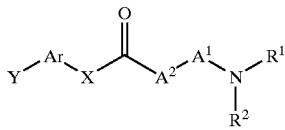

wherein $R^1$ and $R^2$ are each members independently selected from the group consisting of hydrogen, $(C_1-C_2)$alkyl, aryl, aryl$(C_1-C_8)$alkyl, $(C_1-C_8)$heteroalkyl and aryl$(C_1-C_8)$heteroalkyl, with the proviso that at least one of $R^1$ and $R^2$ is selected from the group consisting of aryl, aryl $(C_1-C_8)$alkyl and aryl$(C_1-C_8)$heteroalkyl;

$A^1$ is a member selected from the group consisting of L-α-amino acids, D-α-amino acids and radicals having the formula:

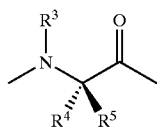

wherein one of $R^4$ and $R^5$ is a member selected from the group consisting of hydrogen, $(C_1-C_8)$alkyl and $(C_1-C_8)$ heteroalkyl, and the other of $R^4$ and $R^5$ combines with $R^3$ to form a 5-, 6-, 7- or 8-membered ring containing from one to three heteroatoms;

$A^2$ is a member selected from the group consisting of L-α-amino acids, D-α-amino acids and radicals having the formula:

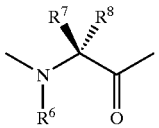

wherein $R^6$ is selected from the group consisting of hydrogen and $(C_1-C_4)$alkyl;

$R^7$ and $R^8$ are each members independently selected from the group consisting of hydrogen, $(C_1-C_8)$alkyl and $(C_1-C_8)$heteroalkyl, or can be combined with each other to form a 5-, 6-, 7- or 8-membered ring containing from zero to three heteroatoms;

X is an unsubstituted $(C_1-C_4)$ saturated or unsaturated alkyl linking group;

Ar is an aryl group; and

Y is a radical selected from the group consisting of:

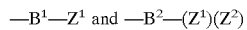

—B¹—Z¹ and —B²—(Z¹)(Z²)

wherein $B^1$ is a bond or a divalent linking group;

$B^2$ is a trivalent linking group;

$Z^1$ is a member selected from the group consisting of —CO₂R⁹, —P(O)(OR⁹)(OR¹⁰), —P(O)(R⁹)(OR¹⁰), —S(O)₂(OR⁹), —S(O)(OR⁹) and a carboxylic acid isostere; and $Z^2$ is a member selected from the group consisting of —CO₂R⁹, —NHR¹¹, —P(O)(OR⁹)(OR¹⁰), —P(O) (R⁹)(OR¹⁰), —S(O)₂(OR⁹), —S(O)(OR⁹) and a carboxylic acid isostere;

wherein $R^9$ and $R^{10}$ are each independently selected from the group consisting of H, $(C_1-C_8)$alkyl, aryl and $(C_1-C_8)$ heteroalkyl; and $R^{11}$ is $(C_1-C_8)$alkyl.

2. A compound of claim 1, wherein $R^1$ and $R^2$ are each members independently selected from the group consisting of aryl and aryl$(C_1-C_8)$alkyl.

3. A compound of claim 1, wherein $R^1$ is an optionally substituted phenyl group.

4. A compound of claim 1, wherein $R^1$ is an optionally substituted phenyl group and $R^2$ is an optionally substituted benzyl group.

5. A compound of claim 1, wherein $R^1$ is an optionally substituted $(C_1-C_8)$alkyl or $(C_1-C_8)$heteroalkyl group and $R^2$ is an optionally substituted phenyl or benzyl group.

6. A compound of claim 1, wherein $R^1$ and $R^2$ are each independently optionally substituted benzyl groups.

7. A compound of claim 1, wherein $R^1$ is a substituted phenyl group selected from 4-tolyl, 4-chlorophenyl, 4-iodophenyl, 4-methoxyphenyl, 4-hydroxyphenyl, 4-carbamoylphenyl, 4-carboxyphenyl and 4-carbomethoxyphenyl.

8. A compound of claim 1, wherein $R^1$ is a phenyl group substituted with up to two members selected from the group consisting of —CONH₂, —CH₂NHCO-(4-nitro-2-pyrazolyl), —CONHPh, —CH₂NH₂, —CH₂NHCO—CH=CH-(3-nitrophenyl), —CH₃, —Cl, —I, —CO₂H, —CO₂CH₃, —OCH₃, —OH, —Ph, —OPh, —CON(CH₃)₂, —C(CH₃)₃, —CH₂NHAc, —CN and —CH₂NHCO—CH=CH-(4-pyridyl).

9. A compound of claim 1, wherein $A^1$ is selected from L-tyrosine, L-serine, L-methionine, L-alanine and L-proline.

10. A compound of claim 1, wherein $A^1$ is a radical having the formula:

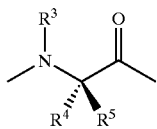

wherein $R^5$ is hydrogen and $R^3$ and $R^4$ are combined to form a 5-, 6-, or 7-membered ring containing from one to three heteroatoms.

11. A compound of claim 10, wherein $A^1$ is a radical selected from the group consisting of

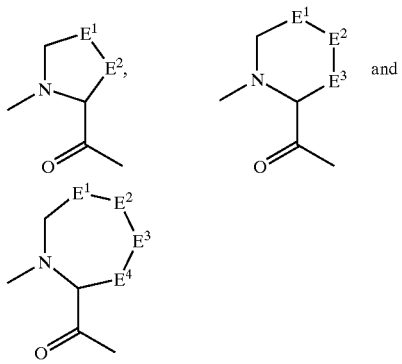

wherein $E^1$, $E^2$, $E^3$ and $E^4$ each independently represent C, N, S or O, with the proviso that the 5-, 6- or 7-membered ring contains no more than three heteroatoms as ring members.

12. A compound of claim 10, wherein $R^3$ and $R^4$ are combined to form a 5-membered ring.

13. A compound of claim 1, wherein $A^1$ is represented by the formula:

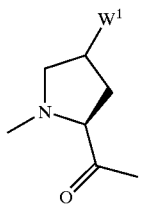

wherein $W^1$ represents a member selected from the group consisting of —$OR^{12}$ and —$NR^{12}R^{13}$ in which $R^{12}$ and $R^{13}$ independently represent a member selected from hydrogen, aryl, $(C_1-C_8)$alkyl, $(C_1-C_8)$heteroalkyl, aryl$(C_1-C_8)$alkyl, aryl$(C_1-C_8)$heteroalkyl, alkylsulfonyl, arylsulfonyl and arylsulfinyl.

14. A compound of claim 1, wherein $A^2$ is selected from L-valine, L-leucine, L-lysine, L-methionine, L-threonine, L-isoleucine and L-tert-butylglycine.

15. A compound of claim 1, wherein $A^2$ is selected from L-valine, L-leucine, L-lysine, L-methionine, L-threonine, L-isoleucine and L-tert-butylglycine, and $R^1$ and $R^2$ are each members independently selected from the group consisting of aryl and aryl$(C_1-C_8)$alkyl.

16. A compound of claim 1, wherein $A^2$ is selected from radicals having the formula:

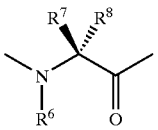

wherein $R^6$ is hydrogen or methyl, $R^8$ is hydrogen, and $R^7$ is selected from methyl, ethyl, n-propyl, isopropyl, n-butyl, sec-butyl, isobutyl and tert-butyl.

17. A compound of claim 15, wherein $A^2$ is L-valine or L-tert-butylglycine.

18. A compound of claim 1, wherein X is selected from —$OCH_2$—, —$CH_2CH_2$—, —CH=CH— and —CH=C($CH_3$)—.

19. A compound of claim 1, wherein Ar represents an optionally substituted benzene ring.

20. A compound of claim 1, wherein Y is —$B^1$—$Z^1$.

21. A compound of claim 20, wherein $B^1$ is selected from a bond, —O—, —$CH_2$—, —CHF—, —CH(OH)—, —$CF_2$—, —$OCH_2$—, —$CH_2CH_2$—, —$CF_2CF_2$—, —$OCF_2$—, —OCHF— and —CHF—CHF—, and $Z^1$ is selected from —$CO_2R^9$, —P(O)($OR^9$)($OR^{10}$), —P(O)($R^9$)($OR^{10}$) and a carboxylic acid isostere.

22. A compound of claim 1, wherein Y is —$B^2$—($Z^1$)($Z^2$).

23. A compound of claim 22, wherein $B^2$ is selected from of —O—CF<, —CH<, —O—CH<, —C(OH)<, —$CH_2$—CH< and —CH=C<, and $Z^1$ and $Z^2$ are each independently selected from —$CO_2R^9$, —P(O)($OR^9$)($OR^{10}$), —P(O)($R^9$)($OR^{10}$) and a carboxylic acid isostere.

24. A compound of claim 1, wherein $R^9$ and $R^{10}$ are each independently selected from hydrogen and $(C_1-C_8)$alkyl.

25. A compound of claim 1, wherein $A^1$ is selected from L-proline and L-alanine, $A^2$ is selected from L-valine, L-leucine, L-isoleucine, L-tert-butylglycine, and $R^1$ and $R^2$ are each members independently selected from the group consisting of aryl and aryl$(C_1-C_8)$alkyl.

26. A compound of claim 1, wherein $A^1$ is selected from L-proline and L-alanine, $A^2$ is selected from L-valine, L-leucine, L-isoleucine, L-tert-butylglycine, $R^1$ is $(C_1-C_8)$alkyl, and $R^2$ is selected from the group consisting of aryl and aryl$(C_1-C_8)$alkyl.

27. A compound of claim 1, wherein $A^1$ is L-proline, $A^2$ is L-tert-butylglycine, and $R^1$ and $R^2$ are each members independently selected from the group consisting of aryl and aryl$(C_1-C_8)$alkyl.

28. A compound of claim 1, wherein $A^1$ is L-proline, $A^2$ is L-tert-butylglycine, $R^1$ is $(C_1-C_8)$alkyl, and $R^2$ is selected from the group consisting of aryl and aryl$(C_1-C_8)$alkyl.

29. A compound of claim 1, wherein $A^1$ is L-proline, $A^2$ is L-tert-butylglycine, X is —CH=CH—, Ar is benzene, $R^1$ and $R^2$ are each members independently selected from the group consisting of aryl and aryl$(C_1-C_8)$alkyl.

30. A compound of claim 1, wherein $A^1$ is L-proline, $A^2$ is L-tert-butylglycine, X is —CH=CH—, Ar is benzene, $R^1$ is $(C_1-C_8)$alkyl, and $R^2$ is selected from the group consisting of aryl and aryl$(C_1-C_8)$alkyl.

31. A compound of claim 1, having the formula:

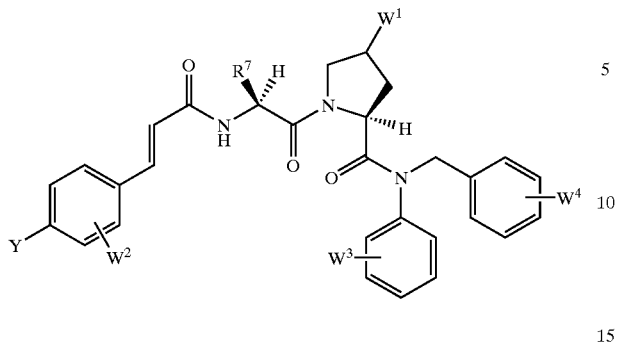

wherein

W¹ represents a member selected from the group consisting of —R$^{12}$ and —NR$^{12}$R$^{13}$;

W², W³ and W⁴ each independently represent a member selected from the group consisting of halogen, —R$^{14}$, —CO$_2$R$^{14}$, —OR$^{14}$, —NR$^{14}$R$^{15}$ and —CONR$^{14}$R$^{15}$;

wherein each of R$^{12}$, R$^{13}$, R$^{14}$ and R$^{15}$ independently represent a member selected from the group consisting of hydrogen, aryl, (C$_1$–C$_8$)alkyl, (C$_1$–C$_8$)heteroalkyl, aryl(C$_1$–C$_8$)alkyl, aryl(C$_1$–C$_8$)heteroalkyl, alkylsulfonyl, arylsulfonyl and arylsulfinyl.

32. A composition comprising an excipient and a compound having the formula:

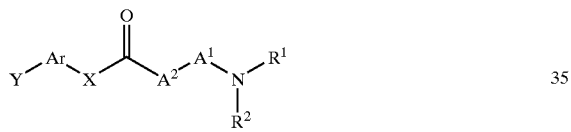

wherein

R¹ and R² are each members independently selected from the group consisting of hydrogen, (C$_1$–C$_8$)alkyl, aryl, aryl(C$_1$–C$_8$)alkyl, (C$_1$–C$_8$)heteroalkyl and aryl(C$_1$–C$_8$)heteroalkyl, with the proviso that at least one of R¹ and R² is selected from the group consisting of aryl, aryl (C$_1$–C$_8$)alkyl and aryl(C$_1$–C$_8$)heteroalkyl;

A¹ is a member selected from the group consisting of L-α-amino acids, D-α-amino acids and radicals having the formula:

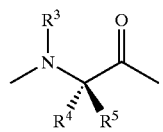

wherein one of R⁴ and R⁵ is a member selected from the group consisting of hydrogen, (C$_1$–C$_8$)alkyl and (C$_1$–C$_8$) heteroalkyl, and the other of R⁴ and R⁵ combines with R³ to form a 5-, 6-, 7- or 8-membered ring containing from one to three heteroatoms;

A² is a member selected from the group consisting of L-α-amino acids, D-α-amino acids and radicals having the formula:

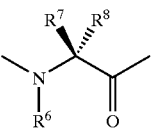

wherein

R⁶ is selected from the group consisting of hydrogen and (C$_1$–C$_4$)alkyl;

R⁷ and R⁸ are each members independently selected from the group consisting of hydrogen, (C$_1$–C$_8$)alkyl and (C$_1$–C$_8$)heteroalkyl, or can be combined with each other to form a 5-, 6-, 7- or 8-membered ring containing from zero to three heteroatoms;

X is an unsubstituted (C$_1$–C$_4$) saturated or unsaturated alkyl linking group;

Ar is an aryl group; and

Y is a radical selected from the group consisting of:

—B¹—Z¹ and —B²—(Z¹)(Z²)

wherein

B¹ is a bond or a divalent linking group;

B² is a trivalent linking group;

Z¹ is a member selected from the group consisting of —CO$_2$R$^9$, —P(O)(OR$^9$)(OR$^{10}$), —P(O)(R$^9$)(OR$^{10}$), —S(O)$_2$(OR$^9$), —S(O)(OR$^9$) and a carboxylic acid isostere; and Z² is a member selected from the group consisting of —CO$_2$R$^9$, —NH$^{11}$, —P(O)(OR$^9$)(OR$^{10}$), —P(O) (R$^9$)(OR$^{10}$, —S(O)$_2$(OR$^9$), —S(O)(OR$^9$) and a carboxylic acid isostere;

wherein

R$^9$ and R$^{10}$ are each independently selected from the group consisting of H, (C$_1$–C$_8$)alkyl, aryl and (C$_1$–C$_8$)heteroalkyl and R$^{11}$ is (C$_1$–C$_8$)alkyl.

33. A composition in accordance with claim 32, wherein R¹ and R² are each members independently selected from the group consisting of aryl and aryl(C$_1$–C$_8$)alkyl.

34. A composition in accordance with claim 32, wherein R¹ is an optionally substituted phenyl group.

35. A composition in accordance with claim 32, wherein R¹ is an optionally substituted phenyl group and R² is an optionally substituted benzyl group.

36. A composition in accordance with claim 32, wherein R¹ is an optionally substituted (C$_1$–C$_8$)alkyl or (C$_1$–C$_8$) heteroalkyl group and R² is an optionally substituted phenyl or benzyl group.

37. A composition in accordance with claim 32, wherein R¹ and R² are each independently optionally substituted benzyl groups.

38. A composition in accordance with claim 32, wherein R¹ is a substituted phenyl group selected from 4-tolyl, 4-chlorophenyl, 4-iodophenyl, 4-methoxyphenyl, 4-hydroxyphenyl, 4-carbamoylphenyl, 4-carboxyphenyl and 4-carbomethoxyphenyl.

39. A composition in accordance with claim 32, wherein R¹ is a phenyl group substituted with up to two members selected from the group consisting of —CONH$_2$, —CH$_2$NHCO-(4-nitro-2-pyrazolyl), —CONHPh, —CH$_2$NH$_2$, —CH$_2$NHCO—CH═CH-(3-nitrophenyl), —CH$_3$, —Cl, —I, —CO$_2$H, —CO$_2$CH$_3$, —OCH$_3$, —OH, —Ph, —OPh, —CON(CH$_3$)$_2$, —C(CH$_3$)$_3$, —CH$_2$NHAc, —CN and —CH$_2$NHCO—CH═CH-(4-pyridyl).

40. A composition in accordance with claim 32, wherein $A^1$ is selected from L-tyrosine, L-serine, L-methionine, L-alanine and L-proline.

41. A composition in accordance with claim 32, wherein $A^1$ is a radical having the formula:

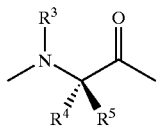

wherein $R^5$ is hydrogen and $R^3$ and $R^4$ are combined to form a 5-, 6-, or 7-membered ring containing from one to three heteroatoms.

42. A composition in accordance with claim 41, wherein $A^1$ is a radical selected from the group consisting of

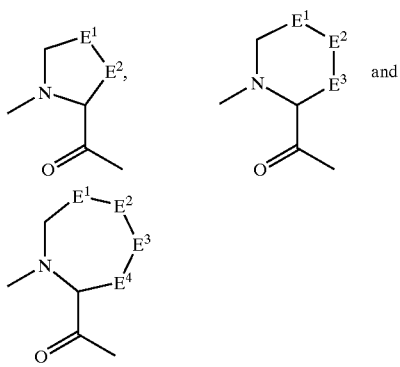

wherein $E^1$, $E^2$, $E^3$ and $E^4$ each independently represent C, N, S or O, with the proviso that the 5-, 6- or 7-membered ring contains no more than three heteroatoms as ring members.

43. A composition in accordance with claim 41, wherein $R^3$ and $R^4$ are combined to form a 5-membered ring.

44. A composition in accordance with claim 32, wherein $A^1$ is represented by the formula:

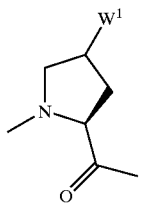

wherein $W^1$ represents a member selected from the group consisting of —$OR^{12}$ and —$NR^{12}R^{13}$ in which $R^{12}$ and $R^{13}$ independently represent a member selected from hydrogen, aryl, ($C_1$–$C_8$)alkyl, ($C_1$–$C_8$)heteroalkyl, aryl($C_1$–$C_8$)alkyl, aryl($C_1$–$C_8$))heteroalkyl, allcylsulfonyl, arylsulfonyl and arylsulfinyl.

45. A composition in accordance with claim 32, wherein $A^2$ is selected from L-valine, L-leucine, L-lysine, L-methionine, L-threonine, L-isoleucine and L-tert-butylglycine.

46. A composition in accordance with claim 32, wherein $A^2$ is selected from L-valine, L-leucine, L-lysine, L-methionine, L-threonine, L-isoleucine and L-tert-butylglycine, and $R^1$ and $R^2$ are each members independently selected from the group consisting of aryl and aryl($C_1$–$C_8$)alkyl.

47. A composition in accordance with claim 32, wherein $A^2$ is selected from radicals having the formula:

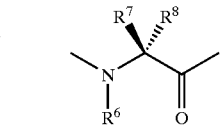

wherein $R^6$ is hydrogen or methyl, $R^8$ is hydrogen, and $R^7$ is selected from methyl, ethyl, n-propyl, isopropyl, n-butyl, sec-butyl, isobutyl and tert-butyl.

48. A composition in accordance with claim 46, wherein $A^2$ is L-valine or L-tert-butylglycine.

49. A composition in accordance with claim 32, wherein X is selected from —$OCH_2$—, —$CH_2CH_2$—, —CH=CH—, and —CH=C($CH_3$)—.

50. A composition in accordance with claim 32, wherein Ar represents an optionally substituted benzene ring.

51. A composition in accordance with claim 32, wherein Y is —$B^1$—$Z^1$.

52. A composition in accordance with claim 51, wherein $B^1$ is selected from a bond, —O—, —$CH_2$—, —CHF—, —CH(OH)—, $CF_2$—, —$OCH_2$—, —$CH_2CH_2$—, —$CF_2CF_2$—, —$OCF_2$—, —OCHF— and —CHF—CHF—, and $Z^1$ is selected from —$CO_2R^9$, —P(O)($OR^9$)($OR^{10}$), —P(O)($R^9$)($OR^{10}$) and a carboxylic acid isostere.

53. A composition in accordance with claim 32, wherein Y is —$B^2$—($Z^1$)($Z^2$).

54. A composition in accordance with claim 53, wherein $B^2$ is selected from of —O—CF<, —CH<, —C(OH)<, —O—CH<, —$CH_2$—CH< and —CH=C<, and $Z^1$ and $Z^2$ are each independently selected from —$CO_2R^9$, —P(O)($OR^9$)($OR^{10}$), —P(O)($R^9$)($OR^{10}$) and a carboxylic acid isostere.

55. A composition in accordance with claim 32, wherein $R^9$ and $R^{10}$ are each independently selected from hydrogen and ($C_1$–$C_8$)alkyl.

56. A composition in accordance with claim 32, wherein $A^1$ is selected from L-proline and L-alanine, $A^2$ is selected from L-valine, L-leucine, L-isoleucine, L-tert-butylglycine, and $R^1$ and $R^2$ are each members independently selected from the group consisting of aryl and aryl($C_1$–$C_8$)alkyl.

57. A composition in accordance with claim 32, wherein $A^1$ is selected from L-proline and L-alanine, $A^2$ is selected from L-valine, L-leucine, L-isoleucine, L-tert-butylglycine, $R^1$ is ($C_1$–$C_8$)alkyl, and $R^2$ is selected from the group consisting of aryl and aryl($C_1$–$C_8$)alkyl.

58. A composition in accordance with claim 32, wherein $A^1$ is L-proline, $A^2$ is L-tert-butylglycine, and $R^1$ and $R^2$ are each members independently selected from the group consisting of aryl and aryl($C_1$–$C_8$)alkyl.

59. A composition in accordance with claim 32, wherein $A^1$ is L-proline, $A^2$ is L-tert-butylglycine, $R^1$ is ($C_1$–$C_8$) alkyl, and $R^2$ is selected from the group consisting of aryl and aryl($C_1$–$C_8$)alkyl.

60. A composition in accordance with claim 32, wherein $A^1$ is L-proline, $A^2$ is L-tert-butylglycine, X is —CH=CH—, Ar is benzene, $R^1$ and $R^2$ are each members independently selected from the group consisting of aryl and aryl($C_1$–$C_8$)alkyl.

61. A composition in accordance with claim 32, wherein $A^1$ is L-proline, $A^2$ is L-tert-butylglycine, X is —CH=CH—, Ar is benzene, $R^1$ is ($C_1$–$C_8$)alkyl, and $R^2$ is selected from the group consisting of aryl and aryl($C_1$–$C_8$) alkyl.

62. A composition in accordance with claim 32, said compound having the formula:

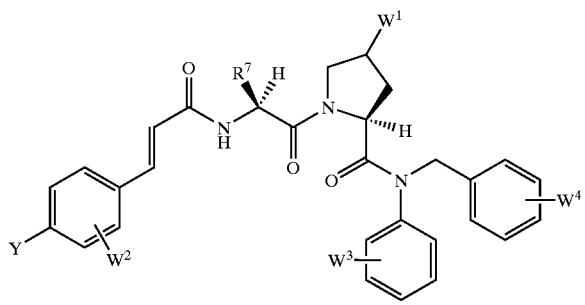

wherein

W$^1$ represents a member selected from the group consisting of —OR$^{12}$ and —NR$^{12}$R$^{13}$;

W$^2$, W$^3$ and W$^4$ each independently represent a member selected from the group consisting of halogen, —R$^{14}$, —CO$_2$R$^{14}$, —OR$^{14}$, —NR$^{14}$R$^{15}$ and —CONR$^{14}$R$^{15}$;

wherein each of R$^{12}$, R$^{13}$, R$^{14}$ and R$^{15}$ independently represent a member selected from the group consisting of hydrogen, aryl, (C$_1$–C$_8$)alkyl, (C$_1$–C$_8$)heteroalkyl, aryl(C$_1$–C$_8$)alkyl, aryl(C$_1$–C$_8$)heteroalkyl, alkylsulfonyl, arylsulfonyl and arylsulfinyl.

* * * * *